(12) United States Patent
Sato

(10) Patent No.: US 8,198,335 B2
(45) Date of Patent: Jun. 12, 2012

(54) COSMETIC MATERIAL

(75) Inventor: Nobumasa Sato, Yokohama (JP)

(73) Assignee: Parahermosa Co., Ltd., Yokohama-shi (JP)

(*) Notice: Subject to any disclaimer, the term of this patent is extended or adjusted under 35 U.S.C. 154(b) by 476 days.

(21) Appl. No.: 12/572,064

(22) Filed: Oct. 1, 2009

(65) Prior Publication Data

US 2010/0087551 A1    Apr. 8, 2010

(51) Int. Cl.
*A61K 8/37* (2006.01)

(52) U.S. Cl. .................... 514/785; 424/400; 424/59

(58) Field of Classification Search .................... None
See application file for complete search history.

(56) References Cited

U.S. PATENT DOCUMENTS

| | | |
|---|---|---|
| 2005/0255057 A1 | 11/2005 | Andre et al. |
| 2007/0025931 A1 | 2/2007 | Goedel et al. |
| 2007/0028401 A1 | 2/2007 | Goedel et al. |
| 2007/0031352 A1 | 2/2007 | Goedel et al. |
| 2007/0160549 A1 | 7/2007 | Hunt et al. |

FOREIGN PATENT DOCUMENTS

| | | |
|---|---|---|
| FR | 2 906 530 A1 | 4/2008 |
| JP | 57-093932 A | 6/1982 |
| JP | 11-071255 A1 | 3/1999 |
| JP | 2000-351721 A1 | 12/2000 |
| JP | 2001-058915 A1 | 3/2001 |
| JP | 2001-270815 A1 | 10/2001 |
| JP | 2004-107349 A1 | 4/2004 |
| JP | 2004-510718 A1 | 4/2004 |
| JP | 2005-513093 A1 | 5/2005 |
| JP | 2005-513094 A1 | 5/2005 |
| JP | 2006-273820 A1 | 10/2006 |
| JP | 2006-281182 A1 | 10/2006 |
| JP | 2007-063164 A1 | 3/2007 |
| JP | 2007-262033 A1 | 10/2007 |
| JP | 2007-277400 A1 | 10/2007 |
| JP | 2007-291025 A1 | 11/2007 |
| JP | 2008-094791 A1 | 4/2008 |
| JP | 2008-106050 A1 | 5/2008 |
| WO | WO 2008/040864 A1 | 4/2008 |

OTHER PUBLICATIONS (Uvinul A Plus) New Stable & Long-lasting UV-A UV Absorbent, www.matsumoto-trd.co.jp/product/pdf/01/15/A.pdf (Searched on Jun. 30, 2008).
"Emollients in Personal Care for Solubilizing Organic UV Absorbers", IP.com Journal, IP.com Inc., West Henrietta, NY, US, Feb. 22, 2006 XP013112931, ISSN: 1533-0001.
European Search Report issued by European Patent Office on Apr. 21, 2010 for the counterpart European Patent Application No. 09 01 2598.

*Primary Examiner* — Johann R. Richter
*Assistant Examiner* — Jessica Kassa
(74) *Attorney, Agent, or Firm* — Knobbe Martens Olson & Bear LLP

(57) ABSTRACT

A cosmetic material includes a component selected from diethyl amino hydroxy benzoyl hexyl benzoate and/or 4-tert-buthyl-4'-methoxy dibenzoyl methane as a component that crystallizes and precipitates easily and blends, as a dissolution stabilizer of the component, one or more types of octyl hydroxy stearate oligomer selected from a dimer to heptamer of octyl hydroxy stearate, whereby precipitation of UV absorbents and other poorly soluble components can be prevented over a long period.

15 Claims, 2 Drawing Sheets

[Fig. 1]

COSMETIC MATERIAL

BACKGROUND OF THE INVENTION

1. Field of the Invention

The present invention relates to a cosmetic material offering excellent sensory characteristics, improved dissolution stability of poorly soluble components such as UV absorbents, excellent compatibility with silicone oil, excellent dispersion stability of pigments and colorants, and excellent safety.

The present invention also relates to a cosmetic material that blends, as a dissolution stabilizer, an octyl hydroxy stearate oligomer selected from a dimer to heptamer of octyl hydroxy stearate (hereinafter simply referred to as "octyl hydroxy stearate oligomer").

More specifically, the present invention relates to a cosmetic material that does not cause separation and precipitation over time of poorly soluble components used in cosmetic materials and known as crystalline long-wavelength UV absorbents that crystallize and precipitate easily during preservation, such as diethyl amino hydroxy benzoyl hexyl benzoate and 4-tert-buthyl-4'-methoxy dibenzoyl methane, and offers excellent UV shielding effect, sensory characteristics, dispersion stability of pigments and colorants, and color development property.

2. Description of Related Art

Traditionally, octyl hydroxy stearate (also known as 2-ethyl hexyl hydroxy stearate) has been a type of oil solution used in cosmetic materials, as described in Patent Literatures 1 to 3. Hydroxy stearate and its oligomer, which are compounds of the same type, are also used in cosmetic materials as described in Patent Literatures 4 to 6.

Hydroxy stearate, which is a source compound of the aforementioned octyl hydroxy stearate, is itself a compound derived from plant-based castor oil. Due in part to the booming use of natural plant-based ingredients in recent years, octyl hydroxy stearate is drawing the attention as a material for making cosmetic products.

As for examples of use of octyl hydroxy stearate, examples of a derivative of hydroxy stearate or its oligomer include zinc 12-hydroxy stearate as described in Patent Literature 7, dipentaerythrityl 12-hydroxy stearate ester, phytosteryl hydroxy stearate and dipentaerythrityl hexa (hydroxy stearate, stearate, rosinate) as described in Patent Literature 8, amide 12-hydroxy stearate as described in Patent Literature 9, polyglycerin ester being a self-condensation product of hydroxy stearate and polyethylene glycol ester also being a self-condensation product of hydroxy stearate as described in Patent Literature 10, and cholesteryl 12-hydroxy stearate as described in Patent Literature 11, all of which are reported as components of cosmetic materials and subject to various examinations.

As described above, hydroxy stearate and its oligomer as well as any derivative thereof, such as octyl hydroxy stearate, are known to be used for cosmetic material applications. However, no examples are found where an oligomer of octyl hydroxy stearate is used for any cosmetic material application.

Being a component used for cosmetic material applications, diethyl amino hydroxy benzoyl hexyl benzoate is known as a UV absorbent because it has a function to absorb long-wavelength UV light. However, its use in cosmetic materials presents problems because diethyl amino hydroxy benzoyl hexyl benzoate is poorly soluble and its crystalline content precipitates in the solution over time.

For example, diethyl amino hydroxy benzoyl hexyl benzoate is mentioned as UV absorbent No. 37 (paragraph 0085) in a cosmetic material disclosed in Patent Literature 12, and also in paragraph 0037 in a UV shielding composition disclosed in Patent Literature 13. In Patent Literature 14, this diethyl amino hydroxy benzoyl hexyl benzoate is made into fine grain powder and blended into a cosmetic material, while in Patent Literature 15 it is blended with 2,4,6-trianilino-p-(carbo-2'-ethyl hexyl-1'-oxy)-1,3,5-triazine and the resulting powder mixture is blended, in a fine powder form, into a cosmetic material.

Since these UV absorbents present problems in terms of their solubility (Patent Literature 15, paragraph 0012), technologies have been reported to convert UV absorbents into nano-powder and blend this nano-powder into a cosmetic materials for the purpose of improving the solubility of these UV absorbents (Patent Literature 16). However, a fundamental problem has been to blend not just diethyl amino hydroxy benzoyl hexyl benzoate, but all UV absorbents, as well, into cosmetic materials in a stable manner without causing dispersion problems.

Diethyl amino hydroxy benzoyl hexyl benzoate has poor solubility in various oil solutions and solvents, and octyl para-methoxy cinnamate (same compound as 2-ethyl hexyl para-methoxy cinnamate) is known as a solvent that can dissolve diethyl amino hydroxy benzoyl hexyl benzoate to a certain degree.

For example, Non-patent Literature 1 shows that diethyl amino hydroxy benzoyl hexyl benzoate dissolves by 42% when 2-ethyl hexyl para-methoxy cinnamate is used as a solvent. However, the solution actually obtained this way presents a problem of diethyl amino hydroxy benzoyl hexyl benzoate crystallizing and precipitating in autumn and winter seasons when temperatures drop.

Non-patent Literature 1 also shows that diethyl amino hydroxy benzoyl hexyl benzoate dissolves only by 0.4% in cyclomethicone, which is a type of volatile silicone.

In Japan and Southeast Asia where the environment is hot and humid, silicone compounds, especially cyclomethicone, are used in large quantities in most sunscreen products for recreational use for the purpose of ensuring resistance to water and sweat. If diethyl amino hydroxy benzoyl hexyl benzoate is blended in sunscreen products used under these conditions, it will precipitate easily. It seems Patent Literatures 14 and 15 mentioned earlier attempted to blend diethyl amino hydroxy benzoyl hexyl benzoate into cosmetic materials without dissolving it, after taking into consideration the fact that diethyl amino hydroxy benzoyl hexyl benzoate is poorly soluble.

As explained above, diethyl amino hydroxy benzoyl hexyl benzoate has poor compatibility with silicone-based cosmetics, and how to improve the solubility of this diethyl amino hydroxy benzoyl hexyl benzoate has been a big problem in the field of cosmetics.

On the other hand, Patent Literatures 17 and 18 introduce a number of examples pertaining to a cosmetic materials in which diethyl amino hydroxy benzoyl hexyl benzoate is blended (brand name: Uvinul A Plus (registered trademark)). However, no methods of manufacturing these examples are shown, and therefore how diethyl amino hydroxy benzoyl hexyl benzoate is dissolved is unknown. In addition, the aforementioned patent literatures use Uvinul A Plus (registered trademark) in powder form, instead of using Uvinul A Plus B (registered trademark) which is another commercially available product constituted by diethyl amino hydroxy benzoyl hexyl benzoate dissolved in octyl para-methoxy cinnamate. Accordingly, whether diethyl amino hydroxy benzoyl hexyl benzoate is actually dissolved is not certain and its stability is not evaluated, either.

As described above, diethyl amino hydroxy benzoyl hexyl benzoate having a function to absorb long-wavelength UV light is in many cases blended as a powder dispersant, as described in Patent Literatures 14 and 15, due to its poor solubility. On the other hand, no means are reported to make diethyl amino hydroxy benzoyl hexyl benzoate more easily soluble.

UV absorbents can be blended in different ways, such as blending into a cosmetic materials as powder or dissolving first and then blending as solution, where in many cases the UV shielding effect per unit blended quantity changes according to the blending method.

In general, the UV shielding effect of a UV absorbent drops when the UV absorbent is blended as powder, compared to when it is dissolved and then blended. This is because when the UV absorbent is blended as powder, gaps are created between powder grains and UV light passes through these gaps to reach the skin, thereby lowering the UV shielding effect in areas where UV light reaches the skin. If the blended quantity of the UV absorbent is the same, a stronger UV shielding effect can be achieved by blending the UV absorbent as solution, and for this reason there is a greater need to use UV absorbents as solution in cosmetic products.

As explained above, cosmetic materials can have a greater UV shielding effect when they blend a UV absorbent in a stable manner, or specifically when they blend a UV absorbent as solution. In addition, the market is also awaiting development of cosmetic products that are resistant to water and sweat, and the needs for UV absorbents suitable in these applications are growing also in the international market.

Just like the problem of poor solubility of the UV absorbent diethyl amino hydroxy benzoyl hexyl benzoate mentioned above, 4-tert-butyl-4'-methoxy dibenzoyl methane which also has a function to shield UV light presents a similar problem.

For example, Patent Literature 19 describes improving the solubility and stability of 4-tert-butyl-4'-methoxy dibenzoyl methane by combining an effective quantity of a silane or organosiloxane compound having a benzylidene camphor functional group and a dibenzoyl methane derivative and then mixing the combined ingredients into a support that can be used in cosmetic products to produce a composition, thereby improving the optical stability and solubility of dibenzoyl methane derivative. On the other hand, Patent Literature 20 describes an optically stable, light-shielding composition for cosmetic or medical use that contains a dibenzoyl methane UV-A shielding agent and p-methoxy cinnamate UV-B shielding agent, where one of the aforementioned shielding agents is incorporated into a polymer matrix.

Furthermore, Patent Literature 21 describes a cosmetic composition for local use for the purpose of protecting skin and/or hair from light, wherein such cosmetic composition contains, in a carrier that can be used in cosmetic products, a target shielding component to be dissolved which is selected from 4-methyl benzylidene camphor (compound A), 4-(tert-butyl)-4'-methoxy dibenzoyl methane (compound B) and a mixture thereof, where such composition is manufactured by dissolving the aforementioned target shielding component to be dissolved through use of a soluble shielding component selected from homomethyl salicylate (compound C), octyl salicylate (compound D) and a mixture thereof, and where enough quantity of this soluble shielding component is used to dissolve all of the aforementioned target shielding component to be dissolved. However, these technologies fail to blend 4-tert-butyl-4'-methoxy dibenzoyl methane in a stable manner in cosmetic formulations with ease, and many examinations are underway to achieve stable blending.

However, cosmetic products currently available on the market only contain a small amount of 4-tert-butyl-4'-methoxy dibenzoyl methane, and the problem has to do with the difficulty in blending a sufficient quantity of 4-tert-butyl-4'-methoxy dibenzoyl methane to achieve a level of stability that warrants industrial applications.

There are many liquid organic UV absorbents that absorb medium-wavelength UV light, few of which present major blending problems that would result in precipitation or crystallization, and therefore no serious problems have been reported so far. As the negative effects of long-wavelength UV light became a point of discussion in recent years, long-wavelength UV absorbents have been drawing the attention. However, not many known components are available that can be used as long-wavelength UV absorbents, and many of these known components are poorly soluble and crystalline in nature. Accordingly, there is an urgent need to study dissolution stabilizers capable of achieving stable dissolution and use, in cosmetic materials, of diethyl amino hydroxy benzoyl hexyl benzoate, 4-tert-butyl-4'-methoxy dibenzoyl methane and other crystalline components that are known as long-wavelength UV absorbents, as described above.

[Patent Literature 1] Japanese Patent Laid-open No. 2001-58915

[Patent Literature 2] Japanese National Publication of Translation No. 2004-510718

[Patent Literature 3] Japanese Patent Laid-open No. 2006-273820

[Patent Literature 4] Japanese Patent Laid-open No. 2008-106050

[Patent Literature 5] Japanese Patent Laid-open No. 2008-94791

[Patent Literature 6] Japanese Patent Laid-open No. 2007-277400

[Patent Literature 7] Japanese Patent Laid-open No. 2007-291025

[Patent Literature 8] Japanese Patent Laid-open No. 2007-262033

[Patent Literature 9] Japanese Patent Laid-open No. 2007-63164

[Patent Literature 10] Japanese Patent Laid-open No. 2006-281182

[Patent Literature 11] Japanese Patent Laid-open No. 2001-270815

[Patent Literature 12] U.S. Patent No. US2005/0255057A1

[Patent Literature 13] U.S. Patent No. US2007/0160549A1

[Patent Literature 14] U.S. Patent No. US2007/0031352A1

[Patent Literature 15] U.S. Patent No. US2007/0028401A1

[Patent Literature 16] U.S. Patent No. US2007/0025931A1

[Patent Literature 17] Published Japanese translation of PCT International Patent Application No. 2005-513093

[Patent Literature 18] Published Japanese translation of PCT International Patent Application No. 2005-513094

[Patent Literature 19] Japanese Patent Laid-open No. 2004-107349

[Patent Literature 20] Japanese Patent Laid-open No. 2000-351721

[Patent Literature 21] Japanese Patent Laid-open No. Hei 11-71255

[Non-patent Literature 1] (Uvinul A Plus) New Stable & Long-lasting UV-A UV Absorbent, www.matsumoto-trd.co.jp/product/pdf/01/15/A.pdf (Searched on Jun. 30, 2008)

SUMMARY

As described in the "Related Art" above, a monomer of octyl hydroxy stearate has been used as a component having good compatibility with various oil solutions.

However, a monomer of octyl hydroxy stearate has not provided a sufficient function as a so-called dissolution stabilizer, or specifically a function to dissolve poorly soluble substances and keep them dissolved in a stable manner over a long period.

For example, a monomer of octyl hydroxy stearate fails to stably dissolve the aforementioned crystalline long-wavelength UV absorbents such as diethyl amino hydroxy benzoyl hexyl benzoate and 4-tert-butyl-4'-methoxy dibenzoyl methane which are representative components difficult to be kept stable once dissolved for use in cosmetic products. To be specific, they may be dissolved temporarily, but crystalline components will precipitate over time. As a result, a monomer of octyl hydroxy stearate could not be used as a dissolution stabilizer for poorly soluble components.

Not only a monomer of octyl hydroxy stearate, but also compounds of the same type such as hydroxy stearate oligomer and hydroxy stearate fail to provide a function as a dissolution stabilizer.

Accordingly, an objective of the present invention is to provide a cosmetic material in which a poorly soluble component used in cosmetic materials and known as a crystalline long-wavelength UV absorbent, such as diethyl amino hydroxy benzoyl hexyl benzoate and 4-tert-butyl-4'-methoxy dibenzoyl methane, remains dissolved in a stable manner over a long period without causing the aforementioned component to separate and precipitate over time, wherein such cosmetic material offers excellent UV shielding effect, sensory characteristics, dispersion stability of pigments and colorants, and color development property.

After earnest studies, the inventors of the present invention found that a formulation offering excellent dissolution stability and temperature stability and undergoing little change over time could be obtained by blending one or more types of an octyl hydroxy stearate oligomer selected from a dimer to heptamer of octyl hydroxy stearate (hereinafter simply referred to as "octyl hydroxy stearate oligomer"; applicant's note) instead of a monomer of octyl hydroxy stearate.

In developing the present invention, the inventors examined how to stably blend diethyl amino hydroxy benzoyl hexyl benzoate and 4-tert-butyl-4'-methoxy dibenzoyl methane, both of which are known as long-wavelength UV absorbents and have been considered difficult to dissolve in a stable manner, by using an octyl hydroxy stearate oligomer and consequently obtained a remarkable success.

As shown by the examples and comparative examples described below, it was confirmed that an octyl hydroxy stearate oligomer would present a marked characteristic to stably dissolve ethyl amino hydroxy benzoyl hexyl benzoate and 4-tert-butyl-4'-methoxy dibenzoyl methane compared to traditionally known oil solutions and that it would also amply meet the practical needs when blended in cosmetic materials.

It was also shown that formulations blended with an octyl hydroxy stearate oligomer would satisfy at high levels such basic characteristics required of cosmetic products as color, smell and other visible factors, skin irritation and other safety factors, temperature stability when heated, etc., touch and other tactile sensations, and compatibility with silicone oil and various other oil solutions.

The first embodiment of the present invention is a cosmetic material characterized in that it blends one or more types of an octyl hydroxy stearate oligomer selected from a dimer to heptamer of octyl hydroxy stearate.

The second embodiment of the present invention is a cosmetic material characterized in that it blends a component that easily crystallizes and precipitates with one or more types of an octyl hydroxy stearate oligomer selected from a dimer to heptamer of octyl hydroxy stearate.

The third embodiment of the present invention is a cosmetic material as mentioned above, characterized in that the octyl hydroxy stearate oligomer is selected from a dimer and/or pentamer.

Based on the present invention, diethyl amino hydroxy benzoyl hexyl benzoate, 4-tert-butyl-4'-methoxy dibenzoyl methane and other long-wavelength absorbents that easily crystallize and precipitate over time while being dissolved in a solution and which are thus difficult to blend into cosmetic materials in a stable manner, can be blended in a stable manner into cosmetic materials by using one or more types of an octyl hydroxy stearate oligomer as a dissolution stabilizer.

In other words, stability, dissolution stability and compatibility with silicone oil of the aforementioned UV absorbents in a formulation can be improved by using one or more types of an octyl hydroxy stearate oligomer as a dissolution stabilizer, and the obtained cosmetic material also offers excellent safety, stability in terms of quality, and sensory characteristics.

DETAILED DESCRIPTION

The present invention is a cosmetic material characterized in that it uses one or more types of an octyl hydroxy stearate oligomer as a dissolution stabilizer. In the context of the present invention, "octyl hydroxy stearate oligomer" refers to a compound produced by octylating a n-mer of hydroxy stearate (where n is selected from 2 (di), 3 (tri), 4 (tetra), 5 (penta), 6 (hexa) and 7 (hepta)).

Traditionally, octyl hydroxy stearate (or strictly "octyl hydroxy stearate monomer") has a structure where n is 1, while the octyl hydroxy stearate oligomer used in the present invention is a dimer to heptamer and thus has a different molecule structure unit.

The octyl hydroxy stearate oligomer used in the present invention is obtained by hydrogenating caster oil to obtain 12-hydroxy stearate, and then causing this 12-hydroxy stearate to self-condensate into a hydroxy stearate oligomer, and finally octylating this hydroxy stearate oligomer. The octyl hydroxy stearate oligomer itself has not been synthesized, and the inventors of the present invention are the first to find utility in these oligomers.

Table 1 shows a comparison of the characteristic values of octyl hydroxy stearate oligomers (dimer to heptamer) used in the present invention against the characteristic values of octyl hydroxy stearate (monomer) and octyl hydroxy stearate oligomer (octamer) which are not included in the scope of the present invention.

Figure 1:
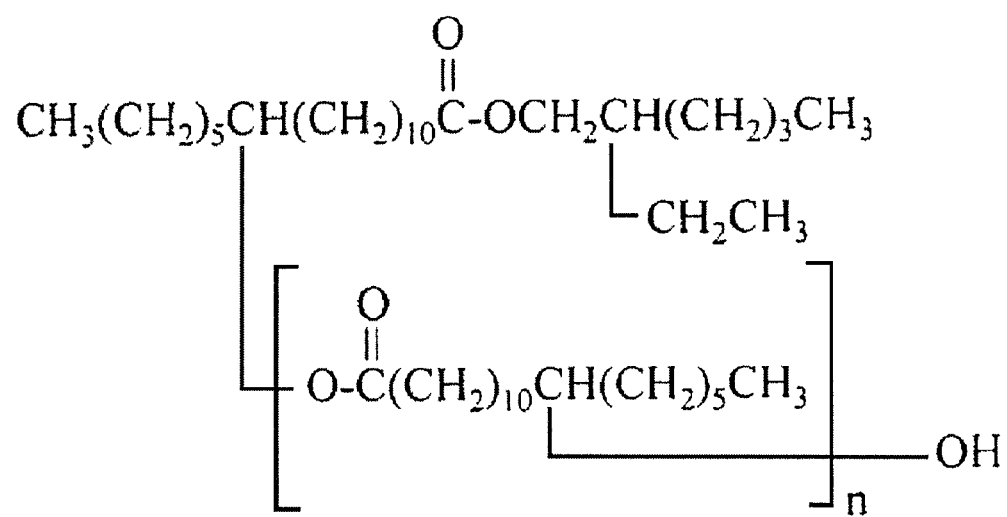
FIG. 1 is Structural formula of an octyl hydroxy stearate oligomer, where n is 1 to 6.
Figure 2:
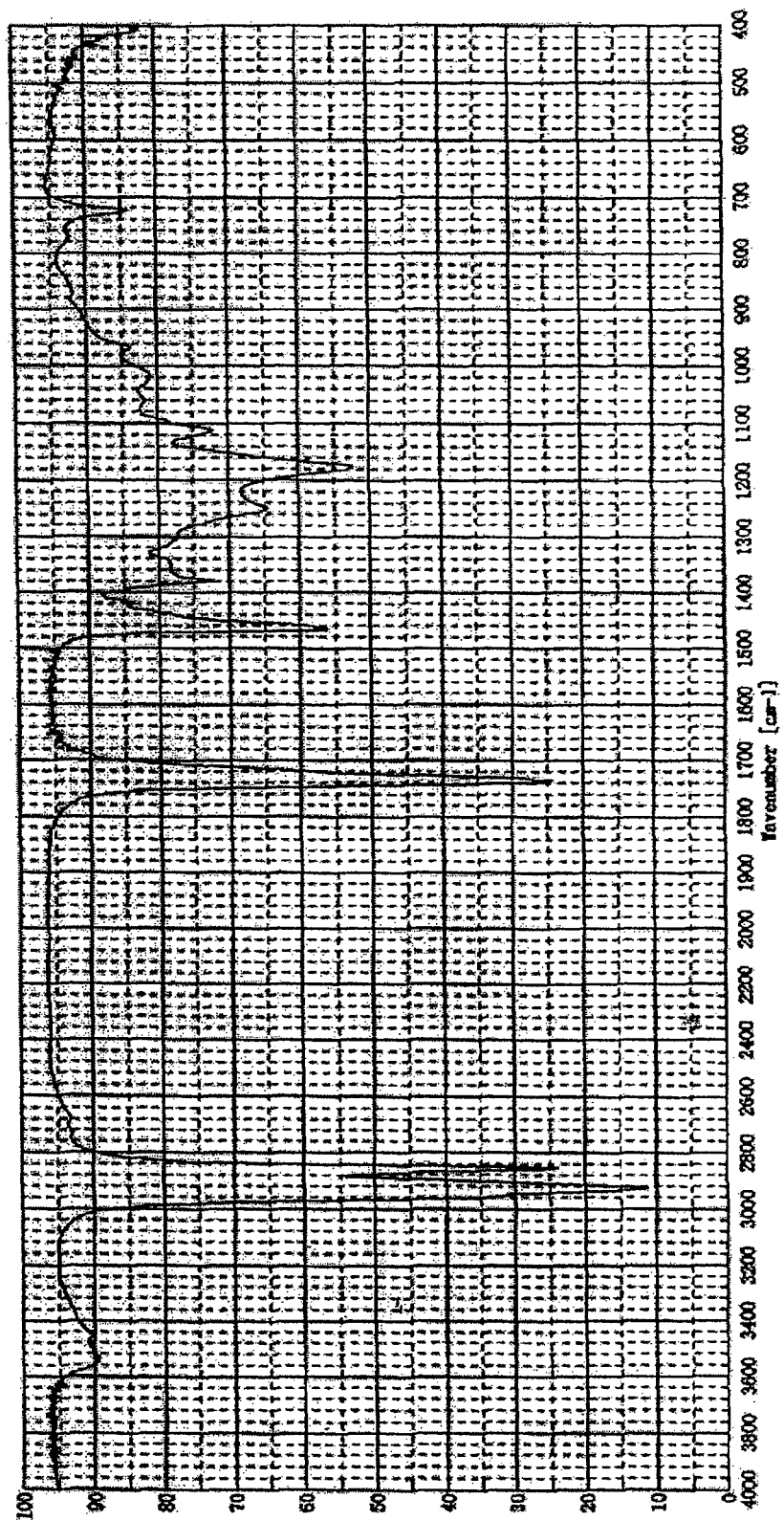
FIG. 2 is Infrared absorption spectrum of an octyl hydroxy stearate oligomer (dimer)

FIG. 1 shows a structural formula of an octyl hydroxy stearate oligomer. FIG. 2 shows an infrared absorption spectrum of a dimer of octyl hydroxy stearate oligomer.

TABLE 1

| Item | Dimer | Trimer | Tetramer | Pentamer | Hexamer | Heptamer | Octamer | Monomer |
|---|---|---|---|---|---|---|---|---|
| Acid value | 0.53 | 1.02 | 1.34 | 2.90 | 1.26 | 2.80 | 4.86 | 0.57 |
| Hydroxyl value | 50.70 | 47.51 | 36.20 | 29.26 | 28.13 | 25.29 | 22.31 | 57.35 |
| Saponification value | 163.20 | 164.30 | 168.96 | 172.27 | 173.96 | 172.96 | 172.84 | 160.31 |
| Refractive index (25° C.) | 1.4577 | 1.4589 | 1.4594 | 1.4596 | 1.4609 | 1.4610 | 1.4610 | 1.4585 |
| Specific gravity (25° C.) | 0.9035 | 0.9027 | 0.9062 | 0.9067 | 0.9060 | 0.9056 | 0.9055 | 0.9024 |
| Viscosity (25° C.) | 152.00 | 180.00 | 260.00 | 305.00 | 307.50 | 294.50 | 278.00 | 162.50 |

As described above, the octyl hydroxy stearate oligomer used in the present invention is one type, or mixture of two or more types, of an octyl hydroxy stearate selected from its dimer to heptamer.

A monomer of octyl hydroxy stearate has problems in terms of stable dissolution of poorly soluble substances, while an octamer and above lead to poor self-condensing property of 12-hydroxy stearate and result in a broad distribution of molecular weight, which in turn causes unstable quality, solidification at temperatures below zero, and undesirable touch and other tactile senstations.

When a monomer of octyl hydroxy stearate is compared with an octyl hydroxy stearate oligomer (dimer to heptamer), differences exist in terms of utility in addition to the effect of stably dissolving diethyl amino hydroxy benzoyl hexyl benzoate, 4-tert-butyl-4'-methoxy dibenzoyl methane and other components that crystallize and precipitate easily as mentioned above.

For example, a monomer of octyl hydroxy stearate is a low-viscosity oil which is non-sticky and has a clean touch and also offers excellent oxidization stability. However, its clouding point is high, or at approx. 20° C., and thus crystal generates in the solution or the entire formulation solidifies in winter, resulting in markedly lower feeling of use and other problems such as the formulation not coming out of the container due to an increased viscosity. An octamer has similar problems.

In cosmetic products, these problems present extremely important quality challenges as they can lead to complaints by consumers. This is why the monomer type, although used for many years, is limited in use.

A dimer of octyl hydroxy stearate is structurally a monomer with one more molecule unit. However, it has substantially different chemical properties. For example, a dimer of octyl hydroxy stearate remains permanently liquid at 5° C., and especially a tetramer and above remain liquid even at −15° C., where feeling of use and low-temperature stability improve dramatically when they are converted to oligomers. The following property has been confirmed: when a monomer of octyl hydroxy stearate is converted to an oligomer, and solids capable of dissolving pigments, colorants and oils, and having low crystalline, are dispersed uniformly, then re-agglutination does not occur easily as compared to a monomer.

This excellent dispersibility of pigments and other coloring materials has significant benefit on the quality of cosmetic products. For example, it improves the color developing property of lipsticks, increases the transparency of liquid foundations, or otherwise contributes significantly to the quality improvement of cosmetic products.

With octyl hydroxy stearate oligomers, the molecular weight distribution is fixed at the time of synthesis and therefore the synthesized oligomer may be refined to obtain a specific n-mer only or a mixture of multiple n-mers.

In the present invention, a dimer to heptamer of octyl hydroxy stearate are used as a dissolution stabilizer when so-called poorly soluble components for cosmetic materials, or components that easily crystallize and precipitate, are used. When the sensory characteristics of the obtained cosmetic material and its stability in the formulation are considered, however, it is desirable to blend a dimer and/or pentamer.

When the aforementioned octyl hydroxy stearate oligomers are used in cosmetic materials, they can be refined to narrow the molecular weight distribution of the applicable oligomer or they can have a distribution of a certain width.

Also, the octyl hydroxy stearate oligomers used in the present invention (dimer to heptamer) can be blended into a cosmetic material to a range of 0.1 to 99 percent by mass, or desirably to a range of 10 to 80 percent by mass, relative to the mass of the cosmetic material.

In the context of the present invention, components that easily crystallize and precipitate include, for example, diethyl amino hydroxy benzoyl hexyl benzoate, 4-tert-butyl-4'-methoxy dibenzoyl methane, ethyl hexyl dimethoxy benzylidene dioxoimidazolidine propionate and other crystalline long-wavelength UV absorbents that absorb long-wavelength UV light of 320 to 400 nm, as well as para-bens (para-oxy benzoate ester), riboflavin tetrabutyrate, ubiquinone and other crystalline components that are solid at normal temperature. The dissolution stabilizers used in the present invention are characterized in that they are highly useful, particularly when used with crystalline long-wavelength UV absorbents.

The cosmetic materials conforming to the present invention use one or more types of the aforementioned octyl hydroxy stearate oligomer as a dissolution stabilizer. As mentioned above, however, the present invention supports blends that contain diethyl amino hydroxy benzoyl hexyl benzoate which is known as a poorly soluble, crystalline long-wavelength UV absorbent.

Diethyl amino hydroxy benzoyl hexyl benzoate is an organic UV absorbent capable of absorbing long-wavelength UV light (320 to 400 nm). One type is sold by BASF under the brand name of Uvinul A Plus, which is solid with a melting point of 50 to 60° C. at normal temperature and pressure. Diethyl amino hydroxy benzoyl hexyl benzoate dissolves in octyl para-methoxy cinnamate by up to 42 percent by mass, but it crystallizes in a low-temperature range of near 5° C. In the presence of a volatile silicone oil such as cyclomethicone or cyclopentasiloxane, diethyl amino hydroxy benzoyl hexyl benzoate crystallizes more easily.

Diethyl amino hydroxy benzoyl hexyl benzoate also presents a problem of crystallizing over time, although it appears to be dissolved temporarily in hydrocarbon oil or ester oil when heated, just like octyl para-methoxy cinnamate used as its solvent.

Although it has excellent UV absorption capability, diethyl amino hydroxy benzoyl hexyl benzoate has been considered a difficult material to blend into cosmetic materials, except when it is blended as powder (the UV absorption efficiency of diethyl amino hydroxy benzoyl hexyl benzoate drops when blended as powder, compared to when blended as solution, as mentioned above; applicant's note), because of its poor solubility and property to crystallize and precipitate over time as mentioned above.

According to the present invention, this diethyl amino hydroxy benzoyl hexyl benzoate which has poor solubility and crystallization/precipitation property can be blended in a stable manner into cosmetic materials, by using an octyl hydroxy stearate oligomer as a dissolution stabilizer for diethyl amino hydroxy benzoyl hexyl benzoate.

To be specific, the inventors of the present invention found that by using this octyl hydroxy stearate oligomer to blend diethyl amino hydroxy benzoyl hexyl benzoate into a cosmetic material, diethyl amino hydroxy benzoyl hexyl benzoate remains stable without crystallizing and even when other general-purpose oil or volatile silicone oil is present, it is dissolved stably and remains dissolved over a long period, and diethyl amino hydroxy benzoyl hexyl benzoate also remains stable without crystallizing even in a cosmetic material blended with its solution.

Just like the diethyl amino hydroxy benzoyl hexyl benzoate mentioned above, 4-tert-butyl-4'-methoxy dibenzoyl methane which is also known as a long-wavelength UV absorbent has presented a similar problem of poor solubility and crystallization and precipitation over time. This problem can also be resolved in the same manner by using the aforementioned octyl hydroxy stearate oligomer as a dissolution stabilizer.

To be specific, 4-tert-butyl-4'-methoxy dibenzoyl methane is an organic UV absorbent capable of absorbing long-wavelength UV light (320 to 400 nm). One type is sold by DSM under the brand name of Parsol 1789. 4-tert-butyl-4'-methoxy dibenzoyl methane is solid at normal temperature and pressure. It crystallizes and precipitates easily and in a formulation 4-tert-butyl-4'-methoxy dibenzoyl methane presents similar problems to those of diethyl amino hydroxy benzoyl hexyl benzoate.

The problem of poor solubility and crystallization/precipitation property resulting from use of this 4-tert-butyl-4'-methoxy dibenzoyl methane could also be resolved in the same manner by using one or more types of an octyl hydroxy stearate oligomer.

As mentioned above, 4-tert-butyl-4'-methoxy dibenzoyl methane is known as a difficult material to blend into cosmetic materials due to its poor solubility. When blended together with an octyl hydroxy stearate oligomer (dimer to heptamer) as proposed by the present invention, however, stable blending of 4-tert-butyl-4'-methoxy dibenzoyl methane into a formulation becomes possible.

To be specific, it has been confirmed that when blended into a cosmetic material based on this combination, 4-tert-butyl-4'-methoxy dibenzoyl methane remains stable without crystallizing and even in the presence of other general-purpose oil or volatile silicone oil, it dissolves stably and remains dissolved over a long period, and 4-tert-butyl-4'-methoxy dibenzoyl methane does not crystallize and remains stable even in a cosmetic materials blended with its solution.

The aforementioned diethyl amino hydroxy benzoyl hexyl benzoate and 4-tert-butyl-4'-methoxy dibenzoyl methane are UV absorbents particularly capable of absorbing long-wavelength UV light, and thus they can be used favorably in UV shielding cosmetic products in combination with UV absorbents capable of absorbing medium-wavelength UV light (290 to 320 nm).

Examples of other UV absorbents used in combination with the aforementioned diethyl amino hydroxy benzoyl hexyl benzoate and 4-tert-butyl-4'-methoxy dibenzoyl methane in cosmetic material conforming to the present invention include: homomethyl salicylate, octyl salicylate, triethanol amine salicylate and other salicylates; para-amino benzoate, ethyl dihydroxy propyl para-amino benzoate, glyceryl para-amino benzoate, octyl dimethyl para-amino benzoate, amyl para-dimethyl amino benzoate, 2-ethyl hexyl para-dimethyl amino benzoate and other PABAs; 4-(2-β-glucopyranosyloxy)propoxy-2-hydroxy benzophenone, dihydroxy dimethoxy benzophenone, sodium dihydroxy dimethoxy benzophenone disulfonate, 2-hydroxy-4-methoxy benzophenone, hydroxy methoxy benzophenone sulfonate and its trihydrate, sodium hydroxy methoxy benzophenone sulfonate, 2-hydroxy-4-methoxy benzophenone-5-sulfate, 2,2'-dihydroxy-4-methoxy benzophenone, 2,4-dihydroxy benzophenone, 2,2',4,4'-tetrahydroxy benzophenone, 2,2'-dihydroxy-4,4'-dimethoxy benzophenone, 2-hydroxy-4-N-octoxy benzophenone and other benzophenones; glyceryl diparamethoxy cinnamate mono-2-ethyl hexanoate, methyl 2,5-diisopropyl cinnamate, 2,4,6-tris[4-(2-ethyl hexyl oxycarbonyl)anilino]-1,3,5-triazine, bis ethyl hexyloxy phenol methixy phenyl triazine, methylene bis benzotriazol yl tetramethyl butyl phenol, trimethoxy cinnamate methyl bis(trimethyl siloxy)silyl isopentyl, isopropyl para-methoxy cinnamate/diisopropyl cinnamate ester mixture, octyl para-methoxy cinnamate, diethanol amine salt of para-methoxy hydro-cinnamate and other cinnamates; 2-phenyl-benzimidazol-5-sulfate, 4-isopropyl dibenzoyl methane and other benzoyl methanes; 2-cyano-3,3-diphenyl prop-2-enoate 2-ethyl hexyl ester (also known as octocrylene), 2-ethyl hexyl dimethoxy benzylidene dioxsoimidazolidine propionate, 1-(3,4-dimethoxy phenyl)-4,4-dimethyl-1,3-pentane dione, cinoxate, methyl-o-amino benzoate, 2-ethyl hexyl-2-cyano-3,3-diphenyl acrylate, 3-(4-methyl benzylidene) camphor, octyl triazone, 2-ethyl hexyl 4-(3,4-dimethoxy phenyl methylene)-2,5-dioxo-1-imidazolidine propionate, as well as polymer derivatives and silane derivatives thereof. Among these, it is particularly desirable that cosmetic materials contain one or more types selected from octyl para-methoxy cinnamate, octocrylene and ethyl hexyl triazone.

With cosmetic materials conforming to the present invention, it is desirable to use an octyl hydroxy stearate oligomer as a dissolution stabilizer to produce beforehand a mixture solution containing the aforementioned diethyl amino hydroxy benzoyl hexyl benzoate, 4-tert-butyl-4'-methoxy dibenzoyl methane and other UV absorbents, as well as other necessary components, and then blend this mixture solution into a cosmetic materials.

This approach has an advantage in that the stability of a component of poor solubility and crystallization/precipitation property can be visually confirmed, as well as other advantage in that problems arising from precipitation, etc., caused by an order of introducing components of cosmetic material can be prevented.

After a mixture solution containing a UV absorbent has been prepared it is desirable to evaluate its stability by filling the mixture solution in a container and storing the container in a thermostatic chamber adjusted to room temperature, 5° C., 40° C., −15° C., etc., and then checking if crystal has precipitated in the stored solution or measuring the spectral distribution of the mixture solution in a UV range of 290 to 400 nm using a SPF Analyzer (registered trademark) or other spectroscopic equipment.

With cosmetic materials conforming to the present invention, the mass blending ratio to be used when the aforementioned mixture solution containing a UV absorbent is blended should be in a range of 0.1 to 100 percent by mass relative to the mass of the cosmetic material, or more preferably in a range of 1 to 80 percent by mass. As long as these ranges are kept, products with high UV shielding effect suitable in a wide range of situations from daily use to recreational use can be obtained.

With cosmetic materials conforming to the present invention, components that are normally blended into cosmetic materials such as silicone oil, oil solution, resin, powder (pigment, colorant, resin), fluorine compound, preservative, fragrance, surface active agent, moisture-preserving agent, bioactive component, salt, solvent, antioxidant, chelating agent, neutralizing agent, pH adjusting agent, thickener, etc., can be used.

Examples of the aforementioned silicone oil include dimethyl polysiloxane, methyl hydrogen polysiloxane, methyl phenyl polysiloxane, polyether denatured organopolysiloxane, fluoroalkyl/polyoxy alkylene co-denatured organopolysiloxane, dimethiconol, end denatured organopolysiloxane, fluorine denatured organopolysiloxane, amodimethicone, amino denatured organopolysiloxane, silicone gel, acryl silicone, volatile silicone (cyclic silicone, methyl trimethicone) and other silicone compounds.

Examples of polyalcohol used as the aforementioned moisture-preserving agent include ethylene glycol, diethylene glycol, polyethylene glycol, propylene glycol, dipropylene glycol, polypropylene glycol, glycerin, diglycerin, polyglycerin, 3-methyl-1,3-butane diol, 1,3-buthylene glycol, sorbitol, mannitol, glucose, sucrose, fructose, xylitol, raffinose, lactose, maltose, maltitol, trehalose, alkylated trehalose, mixed isomerized sugar, sulfated trehalose, pullulan, etc. Chemically modified products of the aforementioned substances can also be used.

Oil solutions that can be used besides octyl hydroxy stearate oligomers under the present invention include volatile and nonvolatile oil solutions, solvents and resins that are normally used in cosmetic materials.

Examples of oil solution include avocado oil, linseed oil, almond oil, olive oil, rhea butter, cacao butter, carnauba wax, candelilla wax, apricot kernel oil, hardend oil, wheat germ oil, sesame oil, rice germ oil, rice bran oil, safflower oil, jojoba wax, serac wax, camellia oil, evening primrose oil, horse oil, castor oil, hardened castor oil, sunflower oil, grape oil, jojoba oil, Macadamia nut oil, bees wax, mink oil, etc.; hydrocarbon oils such as ozokerite, squalane, ceresin, paraffin, synthetic hydrocarbon wax, paraffin wax, liquid paraffin, polyisobutylene, microcrystalline wax, Vaseline, etc.; higher fatty acids such as lauric acid, myristic acid, palmitic acid, stearic acid, behenic acid, undecylenic acid, oleic acid, linoleic acid, linolenic acid, arachidonic acid, eicosapentaenoic acid (EPA), docosahexaenoic acid (DHA), isostearic acid, 12-hydroxy stearic acid, etc.; higher alcohols such as lauryl alcohol, myristyl alcohol, palmityl alcohol, stearyl alcohol, behenyl alcohol, hexadecyl alcohol, oleyl slcohol, isostearyl alcohol, hexyl dodecanol, octyl dodecanol, cetostearyl alcohol, cholesterol, phytosterol, monostearyl glycerin ether (batyl alcohol), monooleyl glyceryl ether (selachyl alcohol), etc.; ester oils such as diisobutyl adipate, 2-hexyl decyl adipate, di-2-heptyl undecyl adipate, N-alkyl glycol monoisostearate, isocetyl isostearate, isononyl isononanate, trimethylol propane triisostearate, ethylene glycol di-2-ethyl hexanoate, cetyl 2-ethyl hexanoate, trimethylol propane tri-2-ethyl hexanoate, pentaerythritol tetra-2-ethyl hexanoate, cetyl octanate, octyl dodecyl gum ester, oleyl oleate, octyl dodecyl oleate, decyl oleate, isononyl isononanate, neopentyl glycol dicaprinate, triethyl citrate, 2-ethyl hexyl succinate, amyl acetate, ethyl acetate, butyl acetate, isocetyl stearate, butyl stearate, diisopropyl sebacate, di-2-ethyl hexyl sebacate, cetyl lactate, myristyl lactate, isopropyl palmitate, 2-ethyl hexyl palmitate, 2-hexyl decyl palmitate, 2-heptyl undecyl palmitate, dipentaerythritol fatty acid ester, isopropyl myristate, octyl dodecyl myristate, 2-hexyl decyl myristate, myristyl myristate, hexyl decyl dimethyl octanoate, ethyl laurate, hexyl laurate, N-lauroyl-L-glutamate-2-octyl dodecyl ester, diisostearyl malate, etc.; glyceride oils such as acetoglyceryl, glyceryl triisooctanoate, glyceryl triisostearate, glycerin tri (capryl/caprate), glyceryl triisopalmitate, glyceryl monostearate, glyceryl di-2-heptyl undecanoate, glyceryl trimyristate, diglyceryl myristate isostearate, ethylene/α-olefin co-oligomer, perfluoropolyether, fluorocarbon, fluoroalcohol and other fluorine compounds, etc.

Examples of powder used in cosmetic materials conforming to the present invention include inorganic powder, organic powder, surface active metal salt powder, colored pigment, pearl pigment, metal powder pigment, tar colorant, natural colorant, etc. To be specific, examples of organic powder include titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, white mica, synthetic mica, gold mica, red mica, black mica, Lithia mica, silicic acid, anhydrous silicate, aluminum silicate, magnesium silicate, aluminum magnesium silicate, calcium silicate, barium silicate, strontium silicate, hydroxy apatite, vermiculite, hydilite, bentonite, montmorillonite, hectorite, zeolite, ceramics powder, calcium phosphate, alumina, aluminum hydroxide, boron nitride, silica, fine-grain titanium oxide, fine-grain zinc oxide, fine-grain cerium oxide, etc.

Examples of the aforementioned powder (pigment, colorant, resin) include organic powders such as polyamide powder, polyester powder, polyethylene powder, polypropylene powder, polystyrene powder, polyurethane powder, benzoguanamine powder, polymethyl benzoguanamine powder, polytetrafluoroethylene powder, polymethyl methacrylate powder, cellulose powder, silk powder, 12 nylon, 6 nylon and other nylon powders, polyacryl powder, polyacryl elastomer, styrene/acrylate copolymer, vinyl resin, urea resin, phenol resin, fluororesin, silicic resin, acryl resin, melamine resin, epoxy resin, fine-crystal fiber powder, starch powder, lauroyl lysine, etc.

Of the aforementioned powders, examples of surface active metal salt powder (metal soap) include zinc stearate, aluminum stearate, calcium stearate, magnesium stearate, zinc myristate, magnesium myristate, zinc cetyl phosphate, calcium cetyl phosphate, zinc sodium cetyl phosphate, etc.

Of the aforementioned powders, examples of colored pigment include iron oxide, iron hydroxide, iron titanate and other inorganic red pigments, γ-iron oxide and other inorganic brown pigments, yellow iron oxide, ocher and other inorganic yellow pigments, black iron oxide, carbon black and other inorganic black pigments, manganese violet, cobalt violet and other inorganic purple pigments, chromium hydroxide, chromium oxide, cobalt oxide, cobalt titanate and other inorganic green pigments, azure, ultramarine and other inorganic blue pigments, laked tar colorant, laked natural colorant, and synthetic resin powder constituted by a mixture of these powders.

Pearl pigments include titanium oxide coated mica, titanium oxide coated mica, bismuth oxychloride, titanium oxide coated bismuth oxychloride, titanium oxide coated talc, scaly foil, titanium oxide coated colored mica, titanium oxide/iron oxide coated mica, etc.; metal powder pigments include aluminum powder, copper powder, stainless powder, etc.; tar colorants include red 3, red 104, red 106, red 201, red 202, red 226, red 228, red 230, red 401, red 505, yellow 4, yellow 5, yellow 202, yellow 203, yellow 204, yellow 401, blue 1, blue 2, blue 201, blue 404, green 3, green 201, green 204, green 205, orange 201, orange 203, orange 204, orange 206, orange 207, etc.; and natural colorants include carminic acid, laccaic acid, carthamin, brazilin, crocin, etc.

The aforementioned powders may or may not be given surface treatment such as water-repelling treatment and hydrophilic treatment.

Examples of surface treatment given to powder include silica treatment, alumina treatment, zinc silicate treatment, silicone treatment, fluorine compound treatment, acryl silicone treatment, acyl amino acid treatment, agar treatment, alginic acid treatment, acrylic acid treatment, metal soap treatment, oil solution treatment, wax treatment, silane treatment, alkyl silane treatment, organic titanate treatment, organic aluminate treatment, silicone resin treatment, silicone elastomer treatment, phosphoryl choline derivative treatment and other traditionally known surface treatments, all of which can be used alone or two or more types can be combined. In particular, there is an advantage in using fine-grain titanium oxide, fine-grain zinc oxide, fine-grain cerium oxide and their water-repellant powder as they produce greater UV shielding effect when used in combination with a UV absorbent solution conforming to the present invention.

Examples of cosmetic materials conforming to the present invention include sunscreen product, makeup base, foundation, concealer, lipstick, lip gloss, eye shadow, nail color, cheek color, cream, milk, beauty essence, conditioner, hair color, body lotion, etc. which can be produced in the forms of multi-layer separation composition, lotion, cream, emulsion, solid, powder, foam, spray, gel, stick, etc.

The present invention is explained in greater details below by using examples. It should be noted, however, that the present invention is not at all limited to these examples.

EXAMPLES

Using diethyl amino hydroxy benzoyl hexyl benzoate as a component of poor solubility and crystallization/precipitation property, one of various types of oil solutions was mixed with diethyl amino hydroxy benzoyl hexyl benzoate being a dissolution stabilizer at a mass ratio of 1:1 and then the mixture was heated to 80° C., filled in a glass container and cooled to room temperature, after which the cooled mixture was placed in a thermostatic chamber adjusted to 5° C. and checked for precipitation of crystal after half a day, one day, one week, and six months.

The results are shown in Table 2.

Evaluation results accompanied by an x in Table 2 indicate that crystal had precipitated at the applicable point in time.

TABLE 2

| Component No. | Component name | Classification | Same day | Following day | 1 week | 6 months |
|---|---|---|---|---|---|---|
| 1 | Octyl hydroxyl stearate oligomer (dimmer) | | | | | ○ |
| 2 | Octyl hydroxyl stearate oligomer (trimer) | | | | | ○ |
| 3 | Octyl hydroxyl stearate oligomer (tetramer) | | | | | ○ |
| 4 | Octyl hydroxyl stearate oligomer (pentamer) | | | | | ○ |
| 5 | Octyl hydroxyl stearate oligomer (hexamer) | | | | | ○ |
| 6 | Octyl hydroxyl stearate oligomer (heptamer) | | | | | ○ |
| 7 | Octyl hydroxy stearate oligomer (dimer:trimer = 2:8) | | | | | ○ |
| 8 | Octyl hydroxy stearate oligomer (dimer:tetramer = 2:8) | | | | | ○ |
| 9 | Octyl hydroxy stearate oligomer (dimer:pentamer = 2:8) | | | | | ○ |
| 10 | Octyl hydroxy stearate oligomer (dimer:hexamer = 2:8) | | | | | ○ |
| 11 | Octyl hydroxy stearate oligomer (dimer:heptamer = 2:8) | | | | | ○ |
| 12 | Octyl hydroxy stearate oligomer (trimer:tetramer = 3:7) | | | | | ○ |
| 13 | Octyl hydroxy stearate oligomer (trimer:pentamer = 3:7) | | | | | ○ |
| 14 | Octyl hydroxy stearate oligomer (trimer:hexamer = 3:7) | | | | | ○ |
| 15 | Octyl hydroxy stearate oligomer (trimer:heptamer = 3:7) | | | | | ○ |
| 16 | Octyl hydroxyl stearate (monomer) | | | | X | |
| 17 | Isotridecyl isononanate | Ester | | | X | |
| 18 | Ethanol (99%) | Lower alcohol | | | X | |
| 19 | Cetyl ethyl hexanoate | Ester | | | X | |
| 20 | Ethyl hexyl palmitate | Ester | | | X | |
| 21 | Glycerin tri 2-ethyl hexanoate | Triglycerin ester | | | X | |
| 22 | DPG | Polyalcohol | X | X | | |
| 23 | Liquid paraffin (C-70) | Hydrocarbon | X | | | |
| 24 | Cyclopentasiloxane | Volatiel silicone | X | | | |
| 25 | Isononyl isononanate | Ester | | X | | |
| 26 | Squalane | Hydrocarbon | X | | | |
| 27 | Dimethicone (20CS) | Silicone | X | | | |
| 28 | Glycerin tri (capryl/caprate) | Triglycerin ester | | X | | |
| 29 | Octyl dodecanol | Higher alcohol | | X | | |
| 30 | Propylene glycol dicaprylate | Ester | | X | | |
| 31 | Glycerin | Polyalcohol | X | | | |
| 32 | 1,3-BG | Polyalcohol | | X | | |
| 33 | Isopropyl palmitate | Ester | X | | | |
| 34 | Octyl dodecyl myristate | Ester | X | | | |

TABLE 2-continued

| Component No. | Component name | Classification | Same day | Following day | 1 week | 6 months |
|---|---|---|---|---|---|---|
| 35 | Sorbitan sesquioleate | Lipophilic surface active agent | | X | | |
| 36 | Sorbitan isostearate | Lipophilic surface active agent | | X | | |
| 37 | Polyoxy ethylene sorbitan trioleate | Hydrophilic surface active agent | | X | | |
| 38 | Polyoxy ethylene sorbitan monooleate | Hydrophilic surface active agent | | X | | |
| 39 | Olive oil | Plant extract oil | X | | | |
| 40 | Jojoba oil | Plant extract oil | X | | | |
| 41 | Sunflower oil | Plant extract oil | | X | | |
| 42 | Caster oil | Plant extract oil | X | | | |
| 43 | PEG-400 | Polyalcohol | X | | | |
| 44 | Ditrimethylol propane triethyl hexanoate | Ester | | X | | |
| 45 | Erythrityl triethyl hexanoate | Ester | | X | | |
| 46 | Ditrimethylol propane (isostearate/sebacate) | Ester | | X | | |
| 47 | Diisostearyl malate | Ester | | X | | |
| 48 | Polypropylene glycol succinate oligo ester | Ester | | X | | |
| 49 | Diglyceryl tetraisostearate | Ester | | X | | |
| 50 | Triethyl hexanoin | Ester | | X | | |
| 51 | Neopentyl glycol diethyl hexanoate | Ester | | X | | |
| 52 | Octyl dodecyl lactate | Ester | | X | | |
| 53 | Neopentyl glycol dicaprylate | Ester | X | | | |
| 54 | Butylene glycol di (capryl/caprate) | Ester | | | X | |
| 55 | Benzylidene malonate polysiloxane | UV absorbent | | X | | |
| 56 | Ethyl hexyl para-methoxy cinnamate | UV absorbent | | | X | |
| 57 | Dicapryl carbonate | Ester | X | | | |
| 58 | Dioctyl ether | Ester | | X | | |
| 59 | Benzophenone-3 | UV absorbent | X | | | |
| 60 | Polyoxy ethylene cetostearyl ether | Hydrophilic surface active agent | X | | | |
| 61 | Stearyl alcohol | Higher alcohol | X | | | |
| 62 | C12-15 alkyl benzoate | UV absorbent | | X | | |
| 63 | Condensed diglyceryl hydroxy stearate | Ester | | X | | |
| 64 | Cyclomethicone | Volatile silicone | X | | | |
| 65 | PEG-40 stearate/polyethylene glycol monostearate | Hydrophilic surface active agent | X | | | |
| 66 | Hydrogenated caster oil dimer dilinoleate | Ester | X | | | |

The results in Table 2 show that crystal precipitated after one week when only a monomer of octyl hydroxy stearate was used.

When an octyl hydroxy stearate oligomer (dimer to heptamer) was used, however, stability was maintained over a long period even when a monomer was also mixed in.

On the other hand, all of various oil solutions traditionally used in cosmetic products crystallized and precipitated and thus presented problems in terms of dissolution stability.

As shown above, it was confirmed that an octyl hydroxy stearate oligomer (dimer to heptamer) conforming to the present invention would provide greater solubility with respect to components of poor solubility and crystallization/precipitation property compared to when any of the various oil solutions traditionally used in cosmetic products was used or a dimer of octyl hydroxy stearate was also mixed in.

Examples 1 to 6

Sunscreen products were produced based on the recipes shown in Table 3 and the manufacturing method specified.

In these examples, tested was combined use of octyl hydroxy stearate oligomer (dimer to heptamer) and diethyl amino hydroxy benzoyl hexyl benzoate being a component of poor solubility and crystallization/precipitation property.

The fields at the bottom show the results of daily observation over six months at 5° C. and room temperature.

Blended quantities are indicated in percent by mass (the same applies hereinafter).

TABLE 3

| No. | Component name | Example 1 | Example 2 | Example 3 | Example 4 | Example 5 | Example 6 | Example 7 |
|---|---|---|---|---|---|---|---|---|
| 1 | Water | 9.84 | 9.84 | 9.84 | 9.84 | 9.84 | 9.84 | 9.84 |
| 2 | Xanthan gum | 0.02 | 0.02 | 0.02 | 0.02 | 0.02 | 0.02 | 0.02 |
| 3 | 1,3-butylene glycol | 5.00 | 5.00 | 5.00 | 5.00 | 5.00 | 5.00 | 5.00 |
| 4 | Methyl para-oxy benzoate | 0.04 | 0.04 | 0.04 | 0.04 | 0.04 | 0.04 | 0.04 |
| 5 | Sorbitan isostearate | 0.60 | 0.60 | 0.60 | 0.60 | 0.60 | 0.60 | 0.60 |
| 6 | Sorbitan sesquioleate | 0.60 | 0.60 | 0.60 | 0.60 | 0.60 | 0.60 | 0.60 |
| 7 | Squalane | 1.60 | 1.60 | 1.60 | 1.60 | 1.60 | 1.60 | 1.60 |
| 8 | Olive oil | 1.60 | 1.60 | 1.60 | 1.60 | 1.60 | 1.60 | 1.60 |
| 9 | Behenic alcohol | 0.30 | 0.30 | 0.30 | 0.30 | 0.30 | 0.30 | 0.30 |
| 10 | Stearic acid | 0.30 | 0.30 | 0.30 | 0.30 | 0.30 | 0.30 | 0.30 |
| 11 | Glyceryl monostearate | 0.10 | 0.10 | 0.10 | 0.10 | 0.10 | 0.10 | 0.10 |

TABLE 3-continued

| No. | Component name | Example 1 | Example 2 | Example 3 | Example 4 | Example 5 | Example 6 | Example 7 |
|---|---|---|---|---|---|---|---|---|
| 12 | Cyclopentasiloxane | 27.00 | 27.00 | 27.00 | 27.00 | 27.00 | 27.00 | 27.00 |
| 13 | Phenyl trimethicone | 22.00 | 22.00 | 22.00 | 22.00 | 22.00 | 22.00 | 22.00 |
| 14 | Titanium oxide | 5.00 | 5.00 | 5.00 | 5.00 | 5.00 | 5.00 | 5.00 |
| 15 | Diethyl amino hydroxy benzoyl hexyl benzoate | 6.00 | 6.00 | 6.00 | 6.00 | 6.00 | 6.00 | 6.00 |
| 16 | Octyl hydroxy stearate oligomer (dimer) | 6.00 | 6.00 | 6.00 | 6.00 | 6.00 | 6.00 | 0.00 |
| 17 | Octyl hydroxy stearate oligomer (trimer) | 14.00 | 0.00 | 0.00 | 0.00 | 0.00 | 0.00 | 0.00 |
| 18 | Octyl hydroxy stearate oligomer (tetramer) | 0.00 | 14.00 | 0.00 | 0.00 | 0.00 | 0.00 | 4.00 |
| 19 | Octyl hydroxy stearate oligomer (pentamer) | 0.00 | 0.00 | 14.00 | 0.00 | 0.00 | 0.00 | 4.00 |
| 20 | Octyl hydroxy stearate oligomer (hexamer) | 0.00 | 0.00 | 0.00 | 14.00 | 0.00 | 0.00 | 4.00 |
| 21 | Octyl hydroxy stearate oligomer (heptamer) | 0.00 | 0.00 | 0.00 | 0.00 | 14.00 | 0.00 | 4.00 |
| | Result of daily observation over 6 months at 5° C. | | | | No abnormality | | | |
| | Result of daily observation over 6 months at room temperature | | | | No abnormality | | | |

<Manufacturing Method>
(1) Emulsify components 1 to 11 at 80° C.
(2) Dissolve component 15 into components 16 to 21 at 80° C. to the extent that transparency is achieved, and cool the mixture to normal temperature.
(3) Add components 12 and 13 to (2) at room temperature and mix well.
(4) Add (3) and component 14 to (1) and mix well, and fill the mixture into a container to obtain a product.

<Evaluation Results> In Examples 1 to 7 where a mixture of a dimer to heptamer of octyl hydroxy stearate oligomer was used, precipitate did not separate after six months of storage at 5° C. or room temperature and no problem was found regarding feeling of use, either.

Examples 8 to 13

Sunscreen products were produced based on the recipes shown in Table 4.

In these examples, tested was use of octyl hydroxy stearate oligomer (dimer to heptamer) as a dissolution stabilizer for diethyl amino hydroxy benzoyl hexyl benzoate, 4-tert-butyl-4'-methoxy dibenzoyl methane or other UV absorbent being a component of poor solubility and crystallization/precipitation property.

Numbers 17 to 20 shown in Table 4 were used as UV absorbents other than diethyl amino hydroxy benzoyl hexyl benzoate and 4-tert-butyl-4'-methoxy dibenzoyl methane.

The results of daily observation over six months at 5° C. and room temperature are shown below.

TABLE 4

| No. | Component name | Example 8 | Example 9 | Example 10 | Example 11 | Example 12 | Example 13 |
|---|---|---|---|---|---|---|---|
| 1 | Water | 9.84 | 9.84 | 9.84 | 9.84 | 9.84 | 9.84 |
| 2 | Xanthan gum | 0.02 | 0.02 | 0.02 | 0.02 | 0.02 | 0.02 |
| 3 | 1,3-butylene glycol | 5.00 | 5.00 | 5.00 | 5.00 | 5.00 | 5.00 |
| 4 | Methyl para-oxy benzoate | 0.04 | 0.04 | 0.04 | 0.04 | 0.04 | 0.04 |
| 5 | Sorbitan isostearate | 0.60 | 0.60 | 0.60 | 0.60 | 0.60 | 0.60 |
| 6 | Sorbitan sesquioleate | 0.60 | 0.60 | 0.60 | 0.60 | 0.60 | 0.60 |
| 7 | Squalane | 1.60 | 1.60 | 1.60 | 1.60 | 1.60 | 1.60 |
| 8 | Olive oil | 1.60 | 1.60 | 1.60 | 1.60 | 1.60 | 1.60 |
| 9 | Behenic alcohol | 0.30 | 0.30 | 0.30 | 0.30 | 0.30 | 0.30 |
| 10 | Stearic acid | 0.30 | 0.30 | 0.30 | 0.30 | 0.30 | 0.30 |
| 11 | Glyceryl monostearate | 0.10 | 0.10 | 0.10 | 0.10 | 0.10 | 0.10 |
| 12 | Cyclopentasiloxane | 27.00 | 27.00 | 27.00 | 27.00 | 27.00 | 27.00 |
| 13 | Phenyl trimethicone | 12.00 | 12.00 | 12.00 | 12.00 | 12.00 | 12.00 |
| 14 | Titanium oxide | 5.00 | 5.00 | 5.00 | 5.00 | 5.00 | 5.00 |
| 15 | Diethyl amino hydroxy benzoyl hexyl benzoate | 6.00 | 6.00 | 6.00 | 6.00 | 6.00 | 6.00 |
| 16 | 4-tert-butyl-4'-methoxy dibenzoyl methane | 2.00 | 2.00 | 2.00 | 2.00 | 2.00 | 2.00 |
| 17 | 2-octyl para-methoxy cinnamate | 5.00 | 5.00 | 5.00 | 5.00 | 5.00 | 5.00 |
| 18 | Octocrylene | 3.00 | 3.00 | 3.00 | 3.00 | 3.00 | 3.00 |
| 19 | Octyl triazone | 2.00 | 2.00 | 2.00 | 2.00 | 2.00 | 2.00 |
| 20 | C12-15 alkyl benzoate | 2.00 | 2.00 | 2.00 | 2.00 | 2.00 | 2.00 |
| 21 | Octyl hydroxy stearate oligomer (dimer) | 16.00 | 0.00 | 0.00 | 0.00 | 0.00 | 0.00 |
| 22 | Octyl hydroxy stearate oligomer (trimer) | 0.00 | 16.00 | 0.00 | 0.00 | 0.00 | 0.00 |
| 23 | Octyl hydroxy stearate oligomer (tetramer) | 0.00 | 0.00 | 16.00 | 0.00 | 0.00 | 0.00 |
| 24 | Octyl hydroxy stearate oligomer (pentamer) | 0.00 | 0.00 | 0.00 | 16.00 | 0.00 | 0.00 |

TABLE 4-continued

| No. | Component name | Example 8 | Example 9 | Example 10 | Example 11 | Example 12 | Example 13 |
|---|---|---|---|---|---|---|---|
| 25 | Octyl hydroxy stearate oligomer (hexamer) | 0.00 | 0.00 | 0.00 | 0.00 | 16.00 | 0.00 |
| 26 | Octyl hydroxy stearate oligomer (heptamer) | 0.00 | 0.00 | 0.00 | 0.00 | 0.00 | 16.00 |
|  | Result of daily observation over 6 months at 5° C. | colspan="6" | No abnormality | | | | |
|  | Result of daily observation over 6 months at room temperature | colspan="6" | No abnormality | | | | |

<Manufacturing Method>
(1) Emulsify components 1 to 11 at 80° C.
(2) Dissolve component 15 into components 16 to 26 at 80° C. to the extent that transparency is achieved, and cool the mixture to normal temperature.
(3) Add components 12 and 13 to (2) at room temperature and mix well.
(4) Add (3) and component 14 to (1) and mix well, and fill the mixture into a container to obtain a product.

<Evaluation Results> In Examples 8 to 13 where a dimer to heptamer of octyl hydroxy stearate oligomer was used, precipitate did not separate after six months of storage at 5° C. or room temperature and no problem was found regarding feeling of use, either.

Comparative Examples 1 to 4

Sunscreen products were produced based on the recipes shown in Table 5.

These comparative examples tested use of octyl hydroxy stearate monomer or octamer as a dissolution stabilizer for diethyl amino hydroxy benzoyl hexyl benzoate or 4-tert-butyl-4'-methoxy dibenzoyl methane being a component of poor solubility and crystallization/precipitation property.

Numbers 17 to 20 shown in Table 4 were used as other UV absorbents.

The results of daily observation over six months at 5° C. and room temperature are also shown in the fields at the bottom.

TABLE 5

| No. | Component name | Comparative Example 1 | Comparative Example 2 | Comparative Example 3 | Comparative Example 4 |
|---|---|---|---|---|---|
| 1 | Water | 9.84 | 9.84 | 9.84 | 9.84 |
| 2 | Xanthan gum | 0.02 | 0.02 | 0.02 | 0.02 |
| 3 | 1,3-butylene glycol | 5.00 | 5.00 | 5.00 | 5.00 |
| 4 | Methyl para-oxy benzoate | 0.04 | 0.04 | 0.04 | 0.04 |
| 5 | Sorbitan isostearate | 0.60 | 0.60 | 0.60 | 0.60 |
| 6 | Sorbitan sesquioleate | 0.60 | 0.60 | 0.60 | 0.60 |
| 7 | Squalane | 1.60 | 1.60 | 1.60 | 1.60 |
| 8 | Olive oil | 1.60 | 1.60 | 1.60 | 1.60 |
| 9 | Behenic alcohol | 0.30 | 0.30 | 0.30 | 0.30 |
| 10 | Stearic acid | 0.30 | 0.30 | 0.30 | 0.30 |
| 11 | Glyceryl monostearate | 0.10 | 0.10 | 0.10 | 0.10 |
| 12 | Cyclopentasiloxane | 27.00 | 27.00 | 27.00 | 27.00 |
| 13 | Phenyl trimethicone | 22.00 | 22.00 | 12.00 | 12.00 |
| 14 | Titanium oxide | 5.00 | 5.00 | 5.00 | 5.00 |
| 15 | Diethyl amino hydroxy benzoyl hexyl benzoate | 6.00 | 6.00 | 6.00 | 6.00 |
| 16 | 4-tert-butyl-4'-methoxy dibenzoyl methane | 0.00 | 0.00 | 2.00 | 2.00 |
| 17 | 2-octyl para-methoxy cinnamate | 0.00 | 0.00 | 5.00 | 5.00 |
| 18 | Octocrylene | 0.00 | 0.00 | 3.00 | 3.00 |
| 19 | Octyl triazone | 0.00 | 0.00 | 2.00 | 2.00 |
| 20 | C12-15 alkyl benzoate | 0.00 | 0.00 | 2.00 | 2.00 |
| 21 | Octyl hydroxy stearate oligomer (monomer) | 20.00 | 0.00 | 16.00 | 0.00 |
| 22 | Octyl hydroxy stearate oligomer (octamer) | 0.00 | 20.00 | 0.00 | 16.00 |
|  | Result of daily observation over 6 months at 5° C. | A large amount of crystal precipitated. | Crystal precipitated. | A large amount of crystal precipitated. | Crystal precipitated. |
|  | Result of daily observation over 6 months at room temperature | Crystal precipitated. | Crystal precipitated. | Crystal precipitated. | Crystal precipitated. |

<Manufacturing Method>
(1) Emulsify components 1 to 11 at 80° C.
(2) Dissolve component 15 into components 16 to 22 at 80° C. to the extent that transparency is achieved, and cool the mixture to normal temperature.
(3) Add components 12 and 13 to (2) at room temperature and mix well.
(4) Add (3) and component 14 to (1) and mix well, and fill the mixture into a container to obtain a product.

<Evaluation Results> When a monomer of octyl hydroxy stearate oligomer was used, crystal separated and precipitated after six months of storage at 5° C. or room temperature, thus failing to meet the quality requirement for cosmetic products.

When an octamer was used, on the other hand, crystal precipitated after six months of storage under both conditions of 5° C. and room temperature, and sensory characteristics also presented problems. This result shows that using an octamer as a dissolution stabilizer would present functional problems.

Ten panelists were asked to apply the sunscreen products obtained in Examples 1 to 13 and Comparative Examples 1 to 4 on their body and face to check the sunburn prevention effect of each product.

The products were evaluated by each panelist based on a five-point scale where 0 represents "Poor" and 5 represents "Excellent," and an average of all scores was calculated and rounded to two decimal places to arrive at the evaluation result.

The results are shown in Table 6.

obtain a cosmetic material by also combining general-purpose oil solutions normally used in cosmetic materials, in order to check if diethyl amino hydroxy benzoyl hexyl benzoate could be blended in a stable manner into the cosmetic materials without being affected by each oil solution.

Each product was manufactured in exactly the same manner as in Example 1, except that each of the oil solutions corresponding to component numbers 16 to 66 in Table 2 was blended by 20.00 percent by mass instead of octyl hydroxy stearate oligomer (dimer or trimer) used in Example 1 as a dissolution stabilizer.

The results are shown in Table 7 below. (The numbers of comparative examples correspond to the order of component numbers in Table 2, respectively.)

<Results> As shown in Table 7 below, all samples obtained in Comparative Examples 5 to 55 presented stability problems as evident from the daily observation over six months at 5° C. and room temperature. This shows that use of other general oil solutions would present problems in achieving stabile dissolution.

On the other hand, stable blending was possible in Example 1, which is clear evidence that the hydroxy stearate oligomer served to substantially improve the blending stability of the formulation.

When Examples 1 to 13 using an octyl hydroxy stearate oligomer (dimer to heptamer) was used as a dissolution stabilizer are compared with Comparative Examples 1 to 55 where no such oligomer was used, it is clear that while all examples conforming to the present invention exhibited

TABLE 6

| Evaluation item | Example 1 | Example 2 | Example 3 | Example 4 | Example 5 | Example 6 | Example 7 | Example 8 | Example 9 |
|---|---|---|---|---|---|---|---|---|---|
| Excellent UV shielding effect | 4.3 | 4.1 | 4.3 | 4.1 | 4.2 | 4.3 | 4.0 | 4.2 | 4.3 |
| Excellent feeling when applied | 4.4 | 4.3 | 4.5 | 4.2 | 4.4 | 4.4 | 4.3 | 4.2 | 4.3 |
| No abnormality is felt on the skin after use | 4.3 | 4.4 | 4.2 | 4.3 | 4.4 | 4.4 | 4.4 | 4.1 | 4.0 |

| Evaluation item | Example 10 | Example 11 | Example 12 | Example 13 | Comparative Example 1 | Comparative Example 2 | Comparative Example 3 | Comparative Example 4 |
|---|---|---|---|---|---|---|---|---|
| Excellent UV shielding effect | 4.0 | 4.1 | 4.2 | 4.3 | 1.2 | 1.6 | 2.2 | 2.3 |
| Excellent feeling when applied | 4.0 | 4.1 | 4.0 | 4.0 | 1.0 | 1.9 | 2.3 | 2.4 |
| No abnormality is felt on the skin after use | 4.3 | 4.2 | 4.3 | 4.1 | 1.9 | 2.0 | 2.0 | 2.2 |

<Evaluation Results> Based on the results shown in Table 6, Examples 1 to 13 blended with a dimer to heptamer of octyl hydroxy stearate oligomer conforming to the present invention, as a dissolution stabilizer, exhibited excellent UV shielding effect and excellent feeling when applied, and presented no safety problems.

On the other hand, Comparative Examples 1 and 3 where octyl hydroxy stearate (monomer) was used were all given a low score. Similarly, both Comparative Examples 2 and 4 where octyl hydroxy stearate (octamer) was used received a low score, as well.

This is likely due to an absence of stable blending of diethyl amino hydroxy benzoyl hexyl benzoate being a component of poor solubility and crystallization/precipitation property.

Comparative Examples 5 to 55

These comparative examples used diethyl amino hydroxy benzoyl hexyl benzoate being a component of poor solubility and crystallization/precipitation property, in a formulation, to excellent stability over time and at low temperature, excellent touch and feeling of use when applied, and presented no problems in terms of ease of use, all comparative examples resulted in precipitation of crystal and presented problems regarding stability over time.

Comparative Examples 56 to 106

These comparative examples checked if 4-tert-butyl-4'-methoxy dibenzoyl methane, being a component of poor solubility and crystallization/precipitation property in the formulation, could be blended in a stable manner.

To be specific, each product was manufactured in exactly the same manner as in Example 7, except that each of the oil solutions corresponding to component numbers 16 to 66 in Table 2 was blended by 16.00 percent by mass instead of octyl hydroxy stearate oligomer (dimer) used in Example 7 as a dissolution stabilizer.

The numbers of comparative examples correspond to the order of component numbers in Table 2, respectively.

The test results are shown in Table 7 below.

TABLE 7

| | | | Evaluation results | | | |
|---|---|---|---|---|---|---|
| | | | Comparative Examples 5 to 55 | | Comparative Examples 56 to 106 | |
| Comparative Example | Comparative Example | Component name | 5° C. | Room temperature | 5° C. | Room temperature |
| 5 | 56 | Octyl hydroxy stearate (monomer) | Precipitation occurred. | Precipitation occurred. | Precipitation occurred. | Precipitation occurred. |
| 6 | 57 | Isotridecyl isononanate | Precipitation occurred. | Precipitation occurred. | Precipitation occurred. | Precipitation occurred. |
| 7 | 58 | Ethanol (99%) | Precipitation occurred. | Precipitation occurred. | Precipitation occurred. | Precipitation occurred. |
| 8 | 59 | Cetyl ethyl hexanoate | Precipitation occurred. | Precipitation occurred. | Precipitation occurred. | Precipitation occurred. |
| 9 | 60 | Ethyl hexyl palmitate | Precipitation occurred. | Precipitation occurred. | Precipitation occurred. | Precipitation occurred. |
| 10 | 61 | Glycerin tri 2-ethyl hexanoate | Precipitation occurred. | Precipitation occurred. | Precipitation occurred. | Precipitation occurred. |
| 11 | 62 | DPG | Precipitation occurred. | Precipitation occurred. | Precipitation occurred. | Precipitation occurred. |
| 12 | 63 | Liquid paraffin (C-70) | Precipitation occurred. | Precipitation occurred. | Precipitation occurred. | Precipitation occurred. |
| 13 | 64 | Cyclopentasiloxane | Precipitation occurred. | Precipitation occurred. | Precipitation occurred. | Precipitation occurred. |
| 14 | 65 | Isononyl isononanate | Precipitation occurred. | Precipitation occurred. | Precipitation occurred. | Precipitation occurred. |
| 15 | 66 | Squalane | Precipitation occurred. | Precipitation occurred. | Precipitation occurred. | Precipitation occurred. |
| 16 | 67 | Dimethicone (20CS) | Precipitation occurred. | Precipitation occurred. | Precipitation occurred. | Precipitation occurred. |
| 17 | 68 | Glycerin tri (capryl/caprate) | Precipitation occurred. | Precipitation occurred. | Precipitation occurred. | Precipitation occurred. |
| 18 | 69 | Octyl dodecanol | Precipitation occurred. | Precipitation occurred. | Precipitation occurred. | Precipitation occurred. |
| 19 | 70 | Propylene glycol dicaprylate | Precipitation occurred. | Precipitation occurred. | Precipitation occurred. | Precipitation occurred. |
| 20 | 71 | Glycerin | Precipitation occurred. | Precipitation occurred. | Precipitation occurred. | Precipitation occurred. |
| 21 | 72 | 1,3-BG | Precipitation occurred. | Precipitation occurred. | Precipitation occurred. | Precipitation occurred. |
| 22 | 73 | Isopropyl palmitate | Precipitation occurred. | Precipitation occurred. | Precipitation occurred. | Precipitation occurred. |
| 23 | 74 | Octyl dodecyl myristate | Precipitation occurred. | Precipitation occurred. | Precipitation occurred. | Precipitation occurred. |
| 24 | 75 | Sorbitan sesquioleate | Precipitation occurred. | Precipitation occurred. | Precipitation occurred. | Precipitation occurred. |
| 25 | 76 | Sorbitan isostearate | Precipitation occurred. | Precipitation occurred. | Precipitation occurred. | Precipitation occurred. |
| 26 | 77 | Polyoxy ethylene sorbitan trioleate | Precipitation occurred. | Precipitation occurred. | Precipitation occurred. | Precipitation occurred. |
| 27 | 78 | Polyoxy ethylene sorbitan monooleate | Precipitation occurred. | Precipitation occurred. | Precipitation occurred. | Precipitation occurred. |
| 28 | 79 | Olive oil | Precipitation occurred. | Precipitation occurred. | Precipitation occurred. | Precipitation occurred. |
| 29 | 80 | Jojoba oil | Precipitation occurred. | Precipitation occurred. | Precipitation occurred. | Precipitation occurred. |
| 30 | 81 | Sunflower oil | Precipitation occurred. | Precipitation occurred. | Precipitation occurred. | Precipitation occurred. |
| 31 | 82 | Caster oil | Precipitation occurred. | Precipitation occurred. | Precipitation occurred. | Precipitation occurred. |
| 32 | 83 | PEG-400 | Precipitation occurred. | Precipitation occurred. | Precipitation occurred. | Precipitation occurred. |
| 33 | 84 | Ditrimethylol propane triethyl hexanoate | Precipitation occurred. | Precipitation occurred. | Precipitation occurred. | Precipitation occurred. |
| 34 | 85 | Erythrityl triethyl hexanoate | Precipitation occurred. | Precipitation occurred. | Precipitation occurred. | Precipitation occurred. |
| 35 | 86 | Ditrimethylol propane (isostearate/sebacate) | Precipitation occurred. | Precipitation occurred. | Precipitation occurred. | Precipitation occurred. |
| 36 | 87 | Diisostearyl malate | Precipitation occurred. | Precipitation occurred. | Precipitation occurred. | Precipitation occurred. |
| 37 | 88 | Polypropylene glycol succinate oligo ester | Precipitation occurred. | Precipitation occurred. | Precipitation occurred. | Precipitation occurred. |
| 38 | 89 | Diglyceryl tetraisostearate | Precipitation occurred. | Precipitation occurred. | Precipitation occurred. | Precipitation occurred. |
| 39 | 90 | Triethyl hexanoin | Precipitation occurred. | Precipitation occurred. | Precipitation occurred. | Precipitation occurred. |

TABLE 7-continued

| | | | Evaluation results | | | |
|---|---|---|---|---|---|---|
| | | | Comparative Examples 5 to 55 | | Comparative Examples 56 to 106 | |
| Comparative Example | Comparative Example | Component name | 5° C. | Room temperature | 5° C. | Room temperature |
| 40 | 91 | Neopentyl glycol diethyl hexanoate | Precipitation occurred. | Precipitation occurred. | Precipitation occurred. | Precipitation occurred. |
| 41 | 92 | Octyl dodecyl lactate | Precipitation occurred. | Precipitation occurred. | Precipitation occurred. | Precipitation occurred. |
| 42 | 93 | Neopentyl glycol dicaprylate | Precipitation occurred. | Precipitation occurred. | Precipitation occurred. | Precipitation occurred. |
| 43 | 94 | Butylene glycol di (capryl/caprate) | Precipitation occurred. | Precipitation occurred. | Precipitation occurred. | Precipitation occurred. |
| 44 | 95 | Benzylidene malonate polysiloxane | Precipitation occurred. | Precipitation occurred. | Precipitation occurred. | Precipitation occurred. |
| 45 | 96 | Ethyl hexyl para-methoxy cinnamate | Precipitation occurred. | Precipitation occurred. | Precipitation occurred. | Precipitation occurred. |
| 46 | 97 | Dicapryl carbonate | Precipitation occurred. | Precipitation occurred. | Precipitation occurred. | Precipitation occurred. |
| 47 | 98 | Dioctyl ether | Precipitation occurred. | Precipitation occurred. | Precipitation occurred. | Precipitation occurred. |
| 48 | 99 | Benzophenone-3 | Precipitation occurred. | Precipitation occurred. | Precipitation occurred. | Precipitation occurred. |
| 49 | 100 | Polyoxy ethylene cetostearyl ether | Precipitation occurred. | Precipitation occurred. | Precipitation occurred. | Precipitation occurred. |
| 50 | 101 | Stearyl alcohol | Precipitation occurred. | Precipitation occurred. | Precipitation occurred. | Precipitation occurred. |
| 51 | 102 | C12-15 alkyl benzoate | Precipitation occurred. | Precipitation occurred. | Precipitation occurred. | Precipitation occurred. |
| 52 | 103 | Condensed diglyceryl hydroxy stearate | Precipitation occurred. | Precipitation occurred. | Precipitation occurred. | Precipitation occurred. |
| 53 | 104 | Cyclomethicone | Precipitation occurred. | Precipitation occurred. | Precipitation occurred. | Precipitation occurred. |
| 54 | 105 | PEG-40 stearate/polyethylene glycol monostearate | Precipitation occurred. | Precipitation occurred. | Precipitation occurred. | Precipitation occurred. |
| 55 | 106 | Hydrogenated caster oil dimer dilinoleate | Precipitation occurred. | Precipitation occurred. | Precipitation occurred. | Precipitation occurred. |

<Evaluation Results> As shown in Table 7, daily observation of Comparative Examples 56 to 106 over six months at 5° C. and room temperature found that all samples exhibited stability problems. This shows that use of other general oil solutions would present problems in achieving stable dissolution.

On the other hand, stable blending was possible in Example 1, which is clear evidence that the hydroxy stearate oligomer served to substantially improve the blending stability of the formulation.

Examples 14 to 19, Comparative Example 107

Lipsticks were produced based on the recipes shown in Table 8 and the manufacturing method specified.

These examples tested color development property of each lipstick when an octyl hydroxy stearate oligomer (dimer to heptamer) was blended into the lipstick as a dissolution stabilizer.

The comparative example tested what would happen when a monomer of octyl hydroxy stearate oligomer was blended.

The results of daily observation over six months at 5° C. and room temperature are also shown in the fields at the bottom.

TABLE 8

| No. | Component name | Example 14 | Example 15 | Example 16 | Example 17 | Example 18 | Example 19 | Comparative Example 107 |
|---|---|---|---|---|---|---|---|---|
| 1 | Synthetic hydrocarbon wax | 6.0 | 6.0 | 6.0 | 6.0 | 6.0 | 6.0 | 6.0 |
| 2 | Microcrystalline wax | 3.0 | 3.0 | 3.0 | 3.0 | 3.0 | 3.0 | 3.0 |
| 3 | Ceresin | 4.0 | 4.0 | 4.0 | 4.0 | 4.0 | 4.0 | 4.0 |
| 4 | Polybutene | 15.0 | 15.0 | 15.0 | 15.0 | 15.0 | 15.0 | 15.0 |
| 5 | Vaseline | 5.0 | 5.0 | 5.0 | 5.0 | 5.0 | 5.0 | 5.0 |
| 6 | Isostearyl alcohol | 3.0 | 3.0 | 3.0 | 3.0 | 3.0 | 3.0 | 3.0 |
| 7 | Octyl dodecyl ricinoleate | 5.0 | 5.0 | 5.0 | 5.0 | 5.0 | 5.0 | 5.0 |
| 8 | Isopropyl isostearate | 3.0 | 3.0 | 3.0 | 3.0 | 3.0 | 3.0 | 3.0 |
| 9 | Squalane | 3.0 | 3.0 | 3.0 | 3.0 | 3.0 | 3.0 | 3.0 |
| 10 | Octyl hydroxy stearate (monomer) | 0.0 | 0.0 | 0.0 | 0.0 | 0.0 | 0.0 | 39.6 |
| 11 | Octyl hydroxy stearate oligomer (dimer) | 39.6 | 0.0 | 0.0 | 0.0 | 0.0 | 0.0 | 0.0 |
| 12 | Octyl hydroxy stearate oligomer (trimer) | 0.0 | 39.6 | 0.0 | 0.0 | 0.0 | 0.0 | 0.0 |

TABLE 8-continued

| No. | Component name | Example 14 | Example 15 | Example 16 | Example 17 | Example 18 | Example 19 | Comparative Example 107 |
|---|---|---|---|---|---|---|---|---|
| 13 | Octyl hydroxy stearate oligomer (tetramer) | 0.0 | 0.0 | 39.6 | 0.0 | 0.0 | 0.0 | 0.0 |
| 14 | Octyl hydroxy stearate oligomer (pentamer) | 0.0 | 0.0 | 0.0 | 39.6 | 0.0 | 0.0 | 0.0 |
| 15 | Octyl hydroxy stearate oligomer (hexamer) | 0.0 | 0.0 | 0.0 | 0.0 | 39.6 | 0.0 | 0.0 |
| 16 | Octyl hydroxy stearate oligomer (heptamer) | 0.0 | 0.0 | 0.0 | 0.0 | 0.0 | 39.6 | 0.0 |
| 17 | Red 201 | 0.5 | 0.5 | 0.5 | 0.5 | 0.5 | 0.5 | 0.5 |
| 18 | Red 202 | 1.5 | 1.5 | 1.5 | 1.5 | 1.5 | 1.5 | 1.5 |
| 19 | Red 104 (1) aluminum lake | 3.0 | 3.0 | 3.0 | 3.0 | 3.0 | 3.0 | 3.0 |
| 20 | Yellow iron oxide | 0.8 | 0.8 | 0.8 | 0.8 | 0.8 | 0.8 | 0.8 |
| 21 | Black iron oxide | 0.1 | 0.1 | 0.1 | 0.1 | 0.1 | 0.1 | 0.1 |
| 22 | Titanium oxide | 1.5 | 1.5 | 1.5 | 1.5 | 1.5 | 1.5 | 1.5 |
| 23 | Titanium mica | 6.0 | 6.0 | 6.0 | 6.0 | 6.0 | 6.0 | 6.0 |

<Manufacturing Method>

(1) Components 1 to 16 were dissolved uniformly at 90° C., after which components 17 to 22 were added and the obtained mixture was passed through a roller.

(2) (1) was dissolved again and when the temperature reached 90° C. or above, component 23 was added and mixed well, after which the mixture was defoamed.

(3) (2) was poured into a die and cooled, and then the solidified product was removed from the die and inserted into a container to obtain a prototype.

<Evaluation Results> The lipsticks obtained in Examples 14 to 19 where a dimer to heptamer of octyl hydroxy stearate was used as an oil solution could be used at 5° C. without presenting any problem. However, the lipstick obtained in Comparative Example 107 using an octyl hydroxy stearate monomer was hard to touch and did not spread well, thus presenting problematic quality.

Accordingly, it was confirmed that octyl hydroxy stearate oligomers would achieve substantially greater dissolution stability with respect to various poorly soluble components used in lipsticks and other cosmetic products, compared to when a monomer of octyl hydroxy stearate was used.

Examples 20 to 27

Lipsticks were produced based on the recipes shown in Table 9 and the manufacturing method specified.

These examples tested color development property of each lipstick when multiple octyl hydroxy stearate oligomers (dimer to heptamer) were combined and blended into the lipstick.

TABLE 9

| No. | Component name | Example 20 | Example 21 | Example 22 | Example 23 | Example 24 | Example 25 | Example 26 | Example 27 |
|---|---|---|---|---|---|---|---|---|---|
| 1 | Synthetic hydrocarbon wax | 6.0 | 6.0 | 6.0 | 6.0 | 6.0 | 6.0 | 6.0 | 6.0 |
| 2 | Microcrystalline wax | 3.0 | 3.0 | 3.0 | 3.0 | 3.0 | 3.0 | 3.0 | 3.0 |
| 3 | Ceresin | 4.0 | 4.0 | 4.0 | 4.0 | 4.0 | 4.0 | 4.0 | 4.0 |
| 4 | Polybutene | 15.0 | 15.0 | 15.0 | 15.0 | 15.0 | 15.0 | 15.0 | 0.0 |
| 5 | Vaseline | 5.0 | 5.0 | 5.0 | 5.0 | 5.0 | 5.0 | 5.0 | 0.0 |
| 6 | Isostearyl alcohol | 3.0 | 3.0 | 3.0 | 3.0 | 3.0 | 3.0 | 3.0 | 0.0 |
| 7 | Octyl dodecyl ricinoleate | 5.0 | 5.0 | 5.0 | 5.0 | 5.0 | 5.0 | 5.0 | 5.0 |
| 8 | Isopropyl isostearate | 3.0 | 3.0 | 3.0 | 3.0 | 3.0 | 3.0 | 3.0 | 0.0 |
| 9 | Squalane | 3.0 | 3.0 | 3.0 | 3.0 | 3.0 | 3.0 | 3.0 | 0.0 |
| 10 | Octyl hydroxy stearate oligomer (dimer) | 15.0 | 15.0 | 15.0 | 15.0 | 15.0 | 24.6 | 24.6 | 24.6 |
| 11 | Octyl hydroxy stearate oligomer (trimer) | 24.6 | 0.0 | 0.0 | 0.0 | 0.0 | 15.0 | 0.0 | 7.0 |
| 12 | Octyl hydroxy stearate oligomer (tetramer) | 0.0 | 24.6 | 0.0 | 0.0 | 0.0 | 0.0 | 0.0 | 12.0 |
| 13 | Octyl hydroxy stearate oligomer (pentamer) | 0.0 | 0.0 | 24.6 | 0.0 | 0.0 | 0.0 | 0.0 | 15.0 |
| 14 | Octyl hydroxy stearate oligomer (hexamer) | 0.0 | 0.0 | 0.0 | 24.6 | 0.0 | 0.0 | 0.0 | 10.0 |
| 15 | Octyl hydroxy stearate oligomer (heptamer) | 0.0 | 0.0 | 0.0 | 0.0 | 24.6 | 0.0 | 15.0 | 10.0 |
| 16 | Red 201 | 0.5 | 0.5 | 0.5 | 0.5 | 0.5 | 0.5 | 0.5 | 0.5 |
| 17 | Red 202 | 1.5 | 1.5 | 1.5 | 1.5 | 1.5 | 1.5 | 1.5 | 1.5 |
| 18 | Red 104 (1) aluminum lake | 3.0 | 3.0 | 3.0 | 3.0 | 3.0 | 3.0 | 3.0 | 3.0 |
| 19 | Yellow iron oxide | 0.8 | 0.8 | 0.8 | 0.8 | 0.8 | 0.8 | 0.8 | 0.8 |
| 20 | Black iron oxide | 0.1 | 0.1 | 0.1 | 0.1 | 0.1 | 0.1 | 0.1 | 0.1 |
| 21 | Titanium oxide | 1.5 | 1.5 | 1.5 | 1.5 | 1.5 | 1.5 | 1.5 | 1.5 |
| 22 | Titanium mica | 6.0 | 6.0 | 6.0 | 6.0 | 6.0 | 6.0 | 6.0 | 6.0 |

<Manufacturing Method>

(1) Components 1 to 15 were dissolved uniformly at 90° C., after which components 16 to 21 were added and the obtained mixture was passed through a roller.

(2) (1) was dissolved again and when the temperature reached 90° C. or above, component 22 was added and mixed well, after which the mixture was defoamed.

(3) (2) was poured into a die and cooled, and then the solidified product was removed from the die and inserted into a container to obtain a prototype.

<Evaluation Results> The lipsticks obtained in Examples 20 to 27 could be used at 5° C. without presenting any problem.

Practical testing was conducted on Examples 14 to 27 (using a dimer to heptamer of octyl hydroxy stearate) and Comparative Example 107 (using a dimer of octyl hydroxy stearate) by asking panelists to evaluate sensory characteristics and color development.

Each of ten panelists gave a score to each evaluation item.

The evaluation standard is as follows: 0 if poor, and 5 if excellent. (Note, however, that the average of all scores was rounded to two decimal places to obtain the final evaluation result.)

The results are shown in Table 10.

<Evaluation Results> Based on the results shown in Table 10, the lipsticks obtained in Examples 14 to 27 (blended with a dimer to heptamer of octyl hydroxy stearate) conforming to the present invention developed excellent color, had excellent feeling when applied, and its safety was also excellent.

On the other hand, the lipstick obtained in Comparative Example 107 (blank) was inferior to any of the lipsticks obtained in the examples in terms of color development.

Examples 28 to 30, Comparative Examples 108 to 110

Lip glosses were produced based on the recipes shown in Table 11 and the manufacturing method specified.

These examples used octyl hydroxy stearate oligomer (dimer to hexamer) as a dissolution stabilizer and compared the color development property and feeling of use against those of comparative examples using a monomer of octyl hydroxy stearate, in terms of the relationship of blended quantity and color development property.

TABLE 10

| Evaluation item | Example 14 | Example 15 | Example 16 | Example 17 | Example 18 | Example 19 | Example 20 | Example 21 |
| --- | --- | --- | --- | --- | --- | --- | --- | --- |
| Excellent color development | 4.4 | 4.3 | 4.4 | 4.6 | 4.5 | 4.2 | 4.4 | 4.5 |
| Excellent feeling when applied | 4.2 | 4.2 | 4.1 | 4.5 | 4.4 | 4.2 | 4.1 | 4.3 |
| No abnormality is felt on the skin after use | 4.7 | 4.5 | 4.6 | 4.6 | 4.4 | 4.3 | 4.3 | 4.5 |

| Evaluation item | Example 22 | Example 23 | Example 24 | Example 25 | Example 26 | Example 27 | Comparative Example 107 |
| --- | --- | --- | --- | --- | --- | --- | --- |
| Excellent color development | 4.8 | 4.5 | 4.3 | 4.4 | 4.3 | 4.5 | 3.4 |
| Excellent feeling when applied | 4.6 | 4.4 | 4.3 | 4.2 | 4.2 | 4.5 | 3.7 |
| No abnormality is felt on the skin after use | 4.8 | 4.6 | 4.5 | 4.7 | 4.6 | 4.7 | 4.4 |

TABLE 11

| No. | Component name | Example 28 | Example 29 | Example 30 | Comparative Example 108 | Comparative Example 109 | Comparative Example 110 |
|---|---|---|---|---|---|---|---|
| 1 | Dextrin palmitate | 8.0 | 0.0 | 0.0 | 8.0 | 0.0 | 0.0 |
| 2 | Synthetic hydrocarbon wax | 0.0 | 4.0 | 4.0 | 0.0 | 4.0 | 4.0 |
| 3 | Octyl dodecyl ricinoleate | 5.0 | 5.0 | 0.0 | 5.0 | 5.0 | 0.0 |
| 4 | Isopropyl isostearate | 5.0 | 5.0 | 0.0 | 5.0 | 5.0 | 0.0 |
| 5 | Octyl dodecyl myristate | 3.0 | 3.0 | 0.0 | 3.0 | 3.0 | 0.0 |
| 6 | Polybutene | 50.0 | 68.0 | 10.0 | 50.0 | 68.0 | 10.0 |
| 7 | Octyl hydroxy stearate (monomer) | 0.0 | 0.0 | 0.0 | 24.0 | 10.0 | 81.0 |
| 8 | Octyl hydroxy stearate oligomer (dimer) | 5.0 | 0.0 | 6.0 | 0.0 | 0.0 | 0.0 |
| 9 | Octyl hydroxy stearate oligomer (trimer) | 0.0 | 0.0 | 5.0 | 0.0 | 0.0 | 0.0 |
| 10 | Octyl hydroxy stearate oligomer (tetramer) | 0.0 | 0.0 | 10.0 | 0.0 | 0.0 | 0.0 |
| 11 | Octyl hydroxy stearate oligomer (pentamer) | 0.0 | 5.0 | 35.0 | 0.0 | 0.0 | 0.0 |
| 12 | Octyl hydroxy stearate oligomer (hexamer) | 19.0 | 5.0 | 25.0 | 0.0 | 0.0 | 0.0 |
| 13 | Titanium mica | 3.0 | 3.0 | 3.0 | 3.0 | 3.0 | 3.0 |
| 14 | Iron oxide coated titanium mica | 2.0 | 2.0 | 2.0 | 2.0 | 2.0 | 2.0 |

<Manufacturing Method>

(1) Components 1 to 12 were dissolved uniformly at 110° C., after which components 13 and 14 were added and dispersed uniformly.

(2) (1) was defoamed and filled in a container to obtain a product.

<Evaluation Results> While the lip glosses obtained in Examples 28 to 30 (octyl hydroxy stearate dimer to hexamer) could be used at 5° C. without presenting any problem, all lip glosses obtained in the comparative examples (monomer of octyl hydroxy stearate) developed specks on the surface, were felt heavy, and all of them had a poor impression.

Examples 31 to 36, Comparative Examples 111 and 112

Oil-based foundations were produced based on the recipes shown in Table 12 and the manufacturing method specified.

These examples tested color development property of oil-based foundation containing an increased amount of organic pigments.

TABLE 12

| No. | Component name | Example 31 | Example 32 | Example 33 | Example 34 | Example 35 | Example 36 | Comparative Example 111 | Comparative Example 112 |
|---|---|---|---|---|---|---|---|---|---|
| 1 | Paraffin | 4.0 | 4.0 | 4.0 | 4.0 | 4.0 | 4.0 | 4.0 | 4.0 |
| 2 | Ceresin | 4.0 | 4.0 | 4.0 | 4.0 | 4.0 | 4.0 | 4.0 | 4.0 |
| 3 | Microcrystalline wax | 6.0 | 6.0 | 6.0 | 6.0 | 6.0 | 6.0 | 6.0 | 6.0 |
| 4 | Synthetic hydrocarbon wax | 6.0 | 6.0 | 6.0 | 6.0 | 6.0 | 6.0 | 6.0 | 6.0 |
| 5 | Octyl dodecanol | 13.0 | 13.0 | 13.0 | 13.0 | 13.0 | 13.0 | 13.0 | 13.0 |
| 6 | Liquid paraffin | 15.6 | 15.6 | 19.6 | 19.6 | 21.6 | 21.6 | 15.6 | 21.6 |
| 7 | Cholesterin stearate | 2.0 | 2.0 | 2.0 | 2.0 | 2.0 | 2.0 | 2.0 | 2.0 |
| 8 | Octyl hydroxy stearate (monomer) | 0.0 | 0.0 | 0.0 | 0.0 | 0.0 | 0.0 | 16.0 | 10.0 |
| 9 | Octyl hydroxy stearate oligomer (dimer) | 16.0 | 0.0 | 0.0 | 0.0 | 0.0 | 0.0 | 0.0 | 0.0 |
| 10 | Octyl hydroxy stearate oligomer (trimer) | 0.0 | 16.0 | 0.0 | 0.0 | 0.0 | 0.0 | 0.0 | 0.0 |
| 11 | Octyl hydroxy stearate oligomer (tetramer) | 0.0 | 0.0 | 12.0 | 0.0 | 0.0 | 0.0 | 0.0 | 0.0 |
| 12 | Octyl hydroxy stearate oligomer (pentamer) | 0.0 | 0.0 | 0.0 | 12.0 | 0.0 | 0.0 | 0.0 | 0.0 |
| 13 | Octyl hydroxy stearate oligomer (hexamer) | 0.0 | 0.0 | 0.0 | 0.0 | 10.0 | 0.0 | 0.0 | 0.0 |
| 14 | Octyl hydroxy stearate oligomer (heptamer) | 0.0 | 0.0 | 0.0 | 0.0 | 0.0 | 10.0 | 0.0 | 0.0 |
| 15 | Titanium oxide | 13.0 | 13.0 | 13.0 | 13.0 | 13.0 | 13.0 | 13.0 | 13.0 |
| 16 | Red iron oxide | 1.0 | 1.0 | 1.0 | 1.0 | 1.0 | 1.0 | 1.0 | 1.0 |
| 17 | Yellow iron oxide | 3.0 | 3.0 | 3.0 | 3.0 | 3.0 | 3.0 | 3.0 | 3.0 |
| 18 | Black iron oxide | 0.4 | 0.4 | 0.4 | 0.4 | 0.4 | 0.4 | 0.4 | 0.4 |
| 19 | Mica | 16.0 | 16.0 | 16.0 | 16.0 | 16.0 | 16.0 | 16.0 | 16.0 |

<Manufacturing Method>

(1) Components 1 to 14 were dissolved uniformly at 90° C., after which components 15 to 19 were added and the obtained mixture was passed through a roller.

(2) (1) was dissolved again and when the temperature reached 90° C., the mixture was defoamed and poured into a container to obtain a product.

<Evaluation Results> While the foundations obtained in Examples 31 to 36 blended with an octyl hydroxy stearate oligomer (dimer to hexamer) could be used at 5° C. without presenting any problem, the foundations obtained in the comparative examples (monomer of octyl hydroxy stearate) were felt hard, did not spread well, and thus exhibited problematic quality.

Example 37, Comparative Example 113

O/W cream foundations were produced based on the recipes shown in Table 13.

This example tested color development property of an O/W cream foundation being a water-based cosmetic product.

TABLE 13

| No. | Component name | Example 37 | Comparative Example 113 |
|---|---|---|---|
| 1 | Purified water | Remaining quantity | Remaining quantity |
| 2 | Native gallant gum | 0.24 | 0.24 |
| 3 | Bentonite | 0.24 | 0.24 |
| 4 | Methyl para-oxy benzoate | 0.20 | 0.20 |
| 5 | Glycerin | 6.00 | 6.00 |
| 6 | Dipropylene glycol | 6.00 | 6.00 |
| 7 | Polyoxy ethylene sorbitan monostearate (20E.0) | 1.50 | 1.50 |
| 8 | Stearic acid | 0.40 | 0.40 |
| 9 | Behenyl alcohol | 0.60 | 0.60 |
| 10 | Sorbitan isostearate | 2.00 | 2.00 |
| 11 | Octyl hydroxy stearate (monomer) | 0.00 | 19.00 |
| 12 | Octyl hydroxy stearate oligomer (trimer) | 13.00 | 0.00 |
| 13 | Octyl hydroxy stearate oligomer (tetramer) | 6.00 | 0.00 |
| 14 | Dimethyl polysiloxane | 5.00 | 5.00 |
| 15 | Titanium oxide | 8.00 | 8.00 |
| 16 | Red iron oxide | 0.36 | 0.36 |
| 17 | Yellow iron oxide | 1.40 | 1.40 |
| 18 | Black iron oxide | 0.25 | 0.25 |

<Manufacturing Method>

(1) Components 2 to 6 were added to component 1 and the mixture was dissolved uniformly at 80° C.

(2) Components 7 to 14 were dissolved uniformly at 80° C.

(3) (2) was added to (1) to achieve emulsification and then components 15 to 18 that had been mixed and crushed beforehand were added and mixed uniformly, after which the mixture was cooled and filled in a tube to obtain a product.

<Evaluation Results> While the foundation obtained in Example 37 (combining both a trimer and tetramer of octyl hydroxy stearate) could be used without presenting any problem, the foundation obtained in Comparative Example 113 (using a monomer of hydroxy stearate) did not come out of the tube easily, was felt hard, did not spread well, and thus exhibited problematic quality.

<Practical Tests> Ten panelists were asked to apply the products obtained in Examples 28 to 37 and Comparative Examples 108 to 113 on their face and lips to test sensory characteristics and color development property. (Refer to the evaluation standard explained earlier.)

The results are shown in Table 14.

TABLE 14

| Evaluation item | Example 28 | Example 29 | Example 30 | Example 31 | Example 32 | Example 33 | Example 34 | Example 35 |
|---|---|---|---|---|---|---|---|---|
| Excellent color development | 4.1 | 4.1 | 4.5 | 4.2 | 4.1 | 4.2 | 4.1 | 4.3 |
| Excellent feeling when applied | 4.3 | 4.2 | 4.8 | 4.1 | 4.1 | 4.3 | 4.2 | 4.2 |
| No abnormality is felt on the skin after use | 4.5 | 4.3 | 4.6 | 4.4 | 4.3 | 4.4 | 4.3 | 4.5 |

| Evaluation item | Example 36 | Example 37 | Comparative Example 108 | Comparative Example 109 | Comparative Example 110 | Comparative Example 111 | Comparative Example 112 | Comparative Example 113 |
|---|---|---|---|---|---|---|---|---|
| Excellent color development | 4.2 | 4.6 | 3.2 | 3.3 | 3.3 | 3.4 | 3.2 | 3.0 |
| Excellent feeling when applied | 4.3 | 4.7 | 3.5 | 3.3 | 3.4 | 3.5 | 3.3 | 3.6 |
| No abnormality is felt on the skin after use | 4.5 | 5.0 | 4.3 | 4.3 | 4.4 | 4.2 | 4.4 | 4.5 |

<Evaluation Results> The results in Table 14 show that all creams obtained in examples conforming to the present invention (dimer to heptamer of hydroxy stearate) developed excellent color, was felt excellent when applied, and their safety was also excellent.

On the other hand, the cream obtained in the comparative examples (hydroxy stearate monomer) showed relatively good performance in terms of feeling when applied and safety, but was inferior to any of the creams obtained in the examples in terms of color development.

Accordingly, it is clear that the octyl hydroxy stearate oligomers were serving to improve the dispersion stability of pigments, improve color development, and also improve the chromatic property and brightness of the cosmetic materials. Also, the results in Table 9 show that color development was improved with both of inorganic pigments and organic pigments.

Examples 38 to 42, Comparative Examples 114 and 115

O/W creams were produced based on the recipes shown in Table 15 and the manufacturing method specified.

These examples tested the effect an octyl hydroxy stearate oligomer would have on sensory characteristics at low temperature.

TABLE 15

| No. | Component name | Example 38 | Example 39 | Example 40 | Example 41 | Example 42 | Comparative Example 114 | Comparative Example 115 |
|---|---|---|---|---|---|---|---|---|
| 1 | Water | Remaining quantity | Remaining quantity | Remaining quantity | Remaining quantity | Remaining quantity | Remaining quantity | Remaining quantity |
| 2 | Glycerin | 4.0 | 4.0 | 4.0 | 4.0 | 4.0 | 4.0 | 4.0 |
| 3 | Dipropylene glycol | 6.0 | 6.0 | 6.0 | 6.0 | 6.0 | 6.0 | 6.0 |
| 4 | Methyl para-oxy benzoate | 0.2 | 0.2 | 0.2 | 0.2 | 0.2 | 0.2 | 0.2 |
| 5 | Polyoxy ethylene sorbitan monostearate | 2.0 | 2.0 | 2.0. | 2.0 | 2.0 | 2.0. | 2.0 |
| 6 | Glyceryl monostearate (self-emulsifying) | 3.5 | 3.5 | 3.5 | 3.5 | 3.5 | 3.5 | 3.5 |
| 7 | Glyceryl myristate | 3.0 | 3.0 | 3.0 | 3.0 | 3.0 | 3.0 | 3.0 |
| 8 | Stearic acid | 4.0 | 4.0 | 4.0 | 4.0 | 4.0 | 4.0 | 4.0 |
| 9 | Octyl hydroxy stearate (monomer) | 0.0 | 0.0 | 0.0 | 0.0 | 0.0 | 15.0 | 8.0 |
| 10 | Octyl hydroxy stearate oligomer (dimer) | 3.0 | 0.0 | 0.0 | 0.0 | 0.0 | 0.0 | 0.0 |
| 11 | Octyl hydroxy stearate oligomer (trimer) | 0.0 | 3.0 | 0.0 | 0.0 | 0.0 | 0.0 | 0.0 |
| 12 | Octyl hydroxy stearate oligomer (tetramer) | 0.0 | 0.0 | 3.0 | 0.0 | 0.0 | 0.0 | 0.0 |
| 13 | Octyl hydroxy stearate oligomer (pentamer) | 0.0 | 12.0 | 0.0 | 5.0 | 0.0 | 0.0 | 0.0 |
| 14 | Octyl hydroxy stearate oligomer (hexamer) | 0.0 | 0.0 | 10.0 | 5.0 | 4.0 | 0.0 | 0.0 |
| 15 | Octyl hydroxy stearate oligomer (heptamer) | 12.0 | 0.0 | 0.0 | 0.0 | 4.0 | 0.0 | 0.0 |
| 16 | Dimethyl polysiloxane | 5.0 | 5.0 | 5.0 | 5.0 | 5.0 | 5.0 | 5.0 |
| 17 | Cyclopentasiloxane | 5.0 | 5.0 | 5.0 | 5.0 | 5.0 | 5.0 | 5.0 |

<Manufacturing Method>

(1) Components 2 to 4 were added to component 1 and dissolved uniformly at 80° C. to the extent that transparency was achieved.

(2) Components 5 to 15 were dissolved uniformly at 80° C.

(3) (2) was added to (1) to achieve emulsification, and then components 16 and 17 were added at 50 to 60° C. or thereabout, after which all components were mixed uniformly and the mixture was cooled to normal temperature and then filled in a tube to obtain a product.

<Evaluation Tests> Ten panelists were asked to apply the creams obtained in Examples 38 to 42 (dimer to heptamer of hydroxy stearate) and Comparative Examples 114 and 115 (monomer of hydroxy stearate) on their face and hand to test sensory characteristics.

The results are shown in Table 16.

TABLE 16

| Evaluation item | Example 38 | Example 39 | Example 40 | Example 41 | Example 42 | Comparative Example 114 | Comparative Example 115 |
|---|---|---|---|---|---|---|---|
| Spread well | 4.2 | 4.5 | 4.4 | 4.5 | 4.6 | 0.0 | 0.0 |
| Absorbed quickly into the skin | 4.3 | 4.2 | 4.3 | 4.3 | 4.4 | 0.0 | 0.0 |
| Skin becomes smooth | 4.0 | 4.1 | 4.3 | 4.2 | 4.3 | 0.0 | 0.0 |

<Evaluation Results> Based on the results shown in Table 16, the creams obtained in examples conforming to the present invention were significantly better than those obtained in comparative examples in terms of spreading, absorption and feeling of application of the cosmetic materials.

In the present disclosure, "the present invention" refers to at least one of the disclosure embodiments or at least one embodiment of the invention. In the present disclosure where conditions and/or structures are not specified, the skilled artisan in the art can readily provide such conditions and/or structures, in view of the present disclosure, as a matter of routine experimentation.

This application claims the priority to Japanese Patent Application No. 2008-259553, filed Oct. 6, 2008, and the disclosure of which is herein incorporated by reference in its entirety.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A cosmetic material characterized by containing a component selected from diethyl amino hydroxy benzoyl hexyl benzoate and/or 4-tert-4'-methoxy dibenzoyl methane as a component that crystallizes and precipitates easily and blending, as a dissolution stabilizer of said component, one or more types of octyl hydroxy stearate oligomer selected from a dimer to heptamer of octyl hydroxy stearate.

2. A cosmetic material according to claim 1, characterized in that the octyl hydroxy stearate oligomer is a dimer and/or pentamer.

3. A cosmetic composition comprising:

(A) a cosmetic material;

(B) diethyl amino hydroxy benzoyl hexyl benzoate and/or 4-tert-buthyl-4'-methoxy dibenzoyl methane as an additive; and (C) one or more types of octyl hydroxy stearate oligomer selected from a dimer to heptamer of octyl hydroxy stearate as a dissolution stabilizer of component (B), wherein components (A), (B), and (C) are blended together.

4. The cosmetic composition according to claim 3, wherein component (B) is a dimer and/or pentamer.

5. The cosmetic composition according to claim 3, wherein components (B) and (C) are homogenously blended.

6. The cosmetic composition according to claim 3, wherein component (C) is contained in an amount effective to inhibit crystallization or precipitation of component (B).

7. The cosmetic composition according to claim 6, wherein component (C) is contained in an amount of 0.1 to 99% by mass relative to the mass of the cosmetic composition.

8. The cosmetic composition according to claim 3, wherein component (B) absorbs long-wavelength UV light of about 320 nm to about 400 nm, and the cosmetic composition further comprises another UV absorbent which absorbs medium-wavelength UV light of about 290 nm to about 320 nm.

9. A cosmetic composition comprising:
a cosmetic material; and
one or more types of octyl hydroxy stearate oligomer selected from a dimer to heptamer of octyl hydroxy stearate as a stabilizer, said one or more types of octyl hydroxyl stearate oligomer being homogenously blended in the cosmetic material.

10. The cosmetic composition according to claim 9, wherein the one or more types of octyl hydroxy stearate oligomer is a dimer and/or pentamer.

11. The cosmetic composition according to claim 10, wherein the one or more types of octyl hydroxy stearate oligomer is contained in an amount of 0.1 to 99% by mass relative to the mass of the cosmetic composition.

12. The cosmetic composition according to claim 11, wherein the one or more types of octyl hydroxy stearate oligomer is contained in an amount of 10 to 80% by mass relative to the mass of the cosmetic composition.

13. The cosmetic composition according to claim 10, further comprising a UV absorbent which absorbs long-wavelength UV light of about 320 nm to about 400 nm.

14. The cosmetic composition according to claim 13, wherein the UV absorbent is diethyl amino hydroxy benzoyl hexyl benzoate and/or 4-tert-buthyl-4'-methoxy dibenzoyl methane.

15. The cosmetic composition according to claim 14, further comprising another UV absorbent which absorbs medium-wavelength UV light of about 290 nm to about 320 nm.

* * * * *

UNITED STATES PATENT AND TRADEMARK OFFICE
CERTIFICATE OF CORRECTION

PATENT NO. : 8,198,335 B2
APPLICATION NO. : 12/572064
DATED : June 12, 2012
INVENTOR(S) : Nobumasa Sato It is certified that error appears in the above-identified patent and that said Letters Patent is hereby corrected as shown below:

On the Title Page, Item (57), Abstract, lines 3-4, delete "4-tert-buthyl-4'-methoxy" and insert therefor --4-tert-butyl-4'-methoxy--.

Column 1, line 24, delete "4-tert-buthyl-4'-methoxy" and insert therefor --4-tert-butyl-4'-methoxy--.

Column 3, line 62, delete "homomethyl" and insert therefor --homomenthyl--.

Column 6, line 35, delete "(dimer)" and insert therefor --(dimer).--.

Column 6, line 52, delete "caster" and insert therefor --castor--.

Column 7, line 22, delete "senstations." and insert therefor --sensations.--.

Column 9, line 67, delete "homomethyl" and insert therefor --homomenthyl--.

Column 10, line 20, delete "methixy" and insert therefor --methoxy--.

Column 10, line 20, delete "bis benzotriazol yl" and insert therefor --dioxoimidazolidine--.

Column 10, line 29, delete "dioxsoimidazolidine" and insert therefor --dioxoimidazolidine--.

Column 11, line 25, delete "1,3-buthylene" and insert therefor --1,3-butylene--.

Column 11, line 37, delete "hardend" and insert therefor --hardened--.

Column 11, line 51, delete "slcohol," and insert therefor --alcohol,--.

Column 11, line 57, delete "isononanate," and insert therefor --isononanoate,--.

Signed and Sealed this
Thirteenth Day of November, 2012

David J. Kappos
*Director of the United States Patent and Trademark Office*

CERTIFICATE OF CORRECTION (continued)
U.S. Pat. No. 8,198,335 B2

Column 11, line 62, delete "isononanate," and insert therefor --isononanoate,--.

Column 12, lines 24-25, delete "hydilite," and insert therefor --hydralite,--.

Columns 13-14, TABLE 2, Component No. 17, Component name, delete "isononanate" and insert therefor --isononanoate--.

Columns 13-14, TABLE 2, Component No. 24, Classification, delete "Volatiel" and insert therefor --Volatile--.

Columns 13-14, TABLE 2, Component No. 25, Component name, delete "isononanate" and insert therefor --isononanoate--.

Columns 15-16, TABLE 2, Component No. 42, Component name, delete "caster" and insert therefor --castor--.

Columns 15-16, TABLE 2, Component No. 66, Component name, delete "caster" and insert therefor --castor--.

Columns 23-24, TABLE 7, Component No. 57, Component name, delete "isononanate" and insert therefor --isononanoate,--.

Columns 23-24, TABLE 7, Component No. 65, Component name, delete "isononanate," and insert therefor --isononanoate,--.

Columns 23-24, TABLE 7, Component No. 82, Component name, delete "caster" and insert therefor --castor--.

Columns 25-26, TABLE 7, Component No. 106, Component name, delete "caster" and insert therefor --castor--.

Column 36, line 42, in Claim 1, delete "4-tert-4'-methoxy" and insert therefor --4-tert-butyl-4'-methoxy--.

Column 36, line 64, in Claim 3, delete "4-tert-buthyl-4'-methoxy" and insert therefor --4-tert-butyl-4'-methoxy--.

Column 38, line 17, in Claim 14, delete "4-tert-buthyl-4'-methoxy" and insert therefor --4-tert-butyl-4'-methoxy--.